(12) United States Patent
Abdolahad et al.

(10) Patent No.: US 11,536,684 B2
(45) Date of Patent: Dec. 27, 2022

(54) ELECTROCHEMICAL METHOD AND DEVICE FOR DETECTING THE EFFECT OF ANTICANCER DRUGS

(71) Applicants: Mohammad Abdolahad, Tehran (IR); Hani Shashaani, Tehran (IR); Mahsa Faramarzpour, Sari (IR)

(72) Inventors: Mohammad Abdolahad, Tehran (IR); Hani Shashaani, Tehran (IR); Mahsa Faramarzpour, Sari (IR)

(73) Assignee: NANO HESGARSAZAN SALAMAT ARYA, Tehran (IR)

( * ) Notice: Subject to any disclaimer, the term of this patent is extended or adjusted under 35 U.S.C. 154(b) by 393 days.

(21) Appl. No.: 16/813,781

(22) Filed: Mar. 10, 2020

(65) Prior Publication Data

US 2020/0209181 A1 Jul. 2, 2020

Related U.S. Application Data

(63) Continuation-in-part of application No. 15/447,415, filed on Mar. 2, 2017, now Pat. No. 10,591,462.

(Continued)

(51) Int. Cl.
*G01N 27/327* (2006.01)
*G01N 27/414* (2006.01)
(Continued)

(52) U.S. Cl.
CPC ..... *G01N 27/3272* (2013.01); *G01N 27/3278* (2013.01); *G01N 27/4065* (2013.01); *G01N 27/4075* (2013.01); *G01N 27/4146* (2013.01)

(58) Field of Classification Search
None
See application file for complete search history.

(56) References Cited

U.S. PATENT DOCUMENTS

2006/0086314 A1* 4/2006 Zhang ............... C30B 29/16
257/E23.025
2009/0017197 A1* 1/2009 Zhang ............... G01N 33/5438
204/403.01

(Continued)

FOREIGN PATENT DOCUMENTS

RU 2460767 C1 * 5/2011 ............. C12M 3/00
WO WO 2010008137 A2 * 1/2010 ............. G01N 33/08

OTHER PUBLICATIONS

Online article by Scott Gordon entitled "New Catalyst does more with less platinum", published Jul. 6, 2015, downloaded Jun. 1, 2022 from https://phys.org/news/2015-07-catalyst-platinum.html (Year: 2015).*

(Continued)

*Primary Examiner* — Alexander S Noguerola
(74) *Attorney, Agent, or Firm* — Bajwa IP Law Firm; Haris Zaheer Bajwa

(57) ABSTRACT

A biosensor for measuring an electrical response from a biological sample. The biosensor includes a substrate, a passivation layer grown on a surface of the substrate, a patterned catalyst layer deposited on the passivation layer, and three electrodes grown on the patterned catalyst layer. The three electrodes include a working electrode, a counter electrode, and a reference electrode. The working electrode includes a first array of electrically conductive biocompatible nanostructures that is configured to be an attachment site for the biological sample. The counter electrode includes a second array of electrically conductive biocompatible nanostructures that is configured to acquire the electrical response from the working electrode. The reference electrode includes a third array of electrically conductive biocompatible nanostructures that is configured to adjust a specific voltage around the working and the counter electrodes.

14 Claims, 32 Drawing Sheets

Related U.S. Application Data

(60) Provisional application No. 62/302,838, filed on Mar. 3, 2016.

(51) Int. Cl.
*G01N 27/407* (2006.01)
*G01N 27/406* (2006.01)

(56) References Cited

U.S. PATENT DOCUMENTS

2009/0297913 A1* 12/2009 Zhang .................. H01M 4/921
  204/403.01
2013/0341185 A1* 12/2013 Collaert ............. G01N 33/4836
  438/49

OTHER PUBLICATIONS

Yoo et al., "An Electrochemical Impedance Measurement Technique Employing Fourier transform,"Anal. Chem. 2000, 72, 2035-2041 (Year: 2000).*
Niwa et al., "Electrochemical Behavior of Reversible Redox Species at Interdigitated Array Electrodes with Different Geometries: Consideration of Redox Cycling and Collection Efficiency," Anal. Chem. 1990, 62, 447-452 (Year: 1990).*
USPTO computer-generated English language translation of Russian patent RU 2460767 C1, effective date for property rights May 10, 2011 (Year: 2011).*
USPTO computer-generated English language translation of WO 2010008137 A2, patent published Jan. 21, 2010. (Year: 2010).*

* cited by examiner

ELECTROCHEMICAL METHOD AND DEVICE FOR DETECTING THE EFFECT OF ANTICANCER DRUGS

CROSS REFERRENCE TO RELATED APPLICATION

This application is a continuation-in-part of U.S. patent application Ser. No. 15/447,415, filed Mar. 2, 2017, and entitled "AN ELECTROCHEMICAL METHOD AND DEVICE FOR DETECTING THE EFFECT OF ANTICANCER DRUGS", which was took priority from U.S. Provisional Patent Application Serial No. 62/302,838, filed Mar. 3, 2016, entitled "Silicon nanowire based electrochemical biosensor with integrated electrodes to detect the drug resistance of cancer cells by label free approach", which are both incorporated herein by reference in their entirety.

TECHNICAL FIELD

The present application generally relates to an electrochemical method for detecting the effect of an anticancer drug on cancer cells using a biosensor including integrated silicon nanowires (hereinafter "SiNWs") electrodes.

BACKGROUND

Electrochemical biosensors transduce biological interactions into detectable electrochemical signals. Biological recognitive markers (e.g. enzymes, aptamers, or antibodies) could be immobilized/integrated at the electrochemical interface to mediate the sensing procedure. However, complexity of chemical modifications and non-specific binding, reduced the reliability and commerciality of such biosensors. If label-free interactions could be applied between analytes and interface, usage of such sensors in wide variety of bio applications would be developed. Such binding must induce changing in electrochemical signal of redox reporter. Moreover, if the oxidative/reductive electrochemical responses of the analyte were unique for different biological transformations (such as metastatic progression states of a cancer cell), sensing patterns would be achieved without any requirements to complex fictionalizations.

Therefore, there is a need for a label-free electrochemical approach with a high precision and fast detecting capability to monitor and detect the electrochemical state variations of cancer cells under cancer treatments such as anticancer drugs treatments.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure is directed to a biosensor for measuring an electrical response from a biological sample. The exemplary biosensor may include a substrate, a passivation layer, a patterned catalyst layer, and three electrodes grown on the patterned catalyst layer. In an exemplary embodiment, the passivation layer may include an electrical passivating layer that may be grown on a surface of the substrate. The patterned catalyst layer may include a patterned catalyst layer that may be deposited on the passivation layer.

In an exemplary embodiment, the three electrodes may include a working electrode, a counter electrode, and a reference electrode. The working electrode may include a first array of electrically conductive biocompatible nanostructures that may be configured to be an attachment site for the biological sample. The counter electrode may include a second array of electrically conductive biocompatible nanostructures that may be configured to acquire the electrical response from the working electrode. The reference electrode may include a third array of electrically conductive biocompatible nanostructures that may be configured to adjust a specific voltage around the working and the counter electrodes.

In an exemplary embodiment, the substrate may include one of a silicon chip and a silicon wafer. In an exemplary embodiment, the passivation layer may include a layer of silicon dioxide ($SiO_2$) with a thickness in a range between 100 nm and 500 nm.

In an exemplary embodiment, the patterned catalyst layer may include a layer of at least one of nickel (Ni), gold (Au), iron (Fe), and combinations thereof. In an exemplary embodiment, the patterned catalyst layer may include a layer of a catalyst with a thickness of less than 10 nm for growing electrically conductive biocompatible nanostructures thereon. In an exemplary embodiment, the patterned catalyst layer may include one of a circular-patterned catalyst layer and an interdigital-patterned catalyst layer.

In an exemplary embodiment, the circular-patterned catalyst layer may include a first semi-circular layer of the catalyst, a second semi-circular layer of the catalyst, and a circular layer of the catalyst. The first semi-circular layer of the catalyst may be deposited and patterned on the passivation layer. The first semi-circular layer of the catalyst may be configured to grow the second array of electrically conductive biocompatible nanostructures thereon. The second semi-circular layer of the catalyst may be deposited and patterned on the passivation layer in front of the first semi-circular layer of the catalyst. The second semi-circular layer of the catalyst may be configured to grow the third array of electrically conductive biocompatible nanostructures thereon. The circular layer of the catalyst may be deposited and patterned on the passivation layer between the first semi-circular layer of the catalyst and the second semi-circular layer of the catalyst. The circular layer of the catalyst may be configured to grow the first array of electrically conductive biocompatible nanostructures thereon.

In an exemplary embodiment, the circular-patterned catalyst layer may include a circular layer of the catalyst, a partially annular layer of the catalyst, and a reference-site layer of the catalyst. The circular layer of catalyst may be deposited and patterned on the passivation layer. The circular layer of the catalyst may be configured to grow the first array of electrically conductive biocompatible nanostructures thereon. The partially annular layer of the catalyst may be deposited and patterned on the passivation layer around the circular layer of the catalyst. The partially annular layer of the catalyst may be configured to grow the second array of electrically conductive biocompatible nanostructures thereon. The reference-site layer of the catalyst may be deposited and patterned on the passivation layer adjacent to both the circular layer of the catalyst and the partially annular layer of the catalyst. The reference-site layer of the catalyst may be configured to grow the third array of electrically conductive biocompatible nanostructures thereon.

In an exemplary embodiment, the interdigital-patterned catalyst layer may include a first teeth-shaped array of the catalyst layer, a second teeth-shaped array of the catalyst layer, and a singular layer of the catalyst. The first teeth-shaped array of the catalyst layer may be deposited and patterned on the passivation layer. The first teeth-shaped array of the catalyst layer may be configured to grow the first array of electrically conductive biocompatible nanostructures thereon. The second teeth-shaped array of the catalyst layer may be deposited and patterned on the passivation layer. The second teeth-shaped array of the catalyst layer may be configured to grow the second array of electrically conductive biocompatible nanostructures thereon. The singular layer of the catalyst may be deposited and patterned on the passivation layer adjacent to the first teeth-shaped array of the catalyst layer and the second teeth-shaped array of the catalyst layer. The singular layer of the catalyst may be configured to grow the third array of electrically conductive biocompatible nanostructures thereon. In an exemplary embodiment, the first teeth-shaped array of the catalyst layer and the second teeth-shaped array of the catalyst layer may be placed inside each other.

In an exemplary embodiment, each of the first teeth-shaped array of the catalyst layer and the second teeth-shaped array of the catalyst layer may include an array of teeth-shaped catalyst layer with a distance between 5 µm and 200 µm for each two teeth patterned next to each other. In an exemplary embodiment, each tooth of the first teeth-shaped array of the catalyst layer and the second teeth-shaped array of the catalyst layer may include a tooth with a width between 5 µm and 200 µm. In an exemplary embodiment, each tooth of the first teeth-shaped array of the catalyst layer may be placed next to at least one tooth of the second teeth-shaped array of the catalyst layer. In an exemplary embodiment, a distance between each tooth of the first teeth-shaped array of the catalyst layer and an adjacent tooth of the second teeth-shaped array of the catalyst layer may be the same as the width of each teeth.

In an exemplary embodiment, the electrically conductive biocompatible nanostructures may include at least one of silicon nanowires (SiNWs), silicon nanograss, carbon nanotubes (CNTs), and combinations thereof. In an exemplary embodiment, the SiNWs may include a plurality of SiNWs with a width of less than 80 nm and a length of less than 50 µm. In an exemplary embodiment, the CNTs may include a plurality of vertically aligned multi-walled carbon nanotubes (VAMWCNTs) with a length of between 0.5 µm and 10 µm and a diameter of between 20 nm and 100 nm.

DETAILED DESCRIPTION

Figure 1:
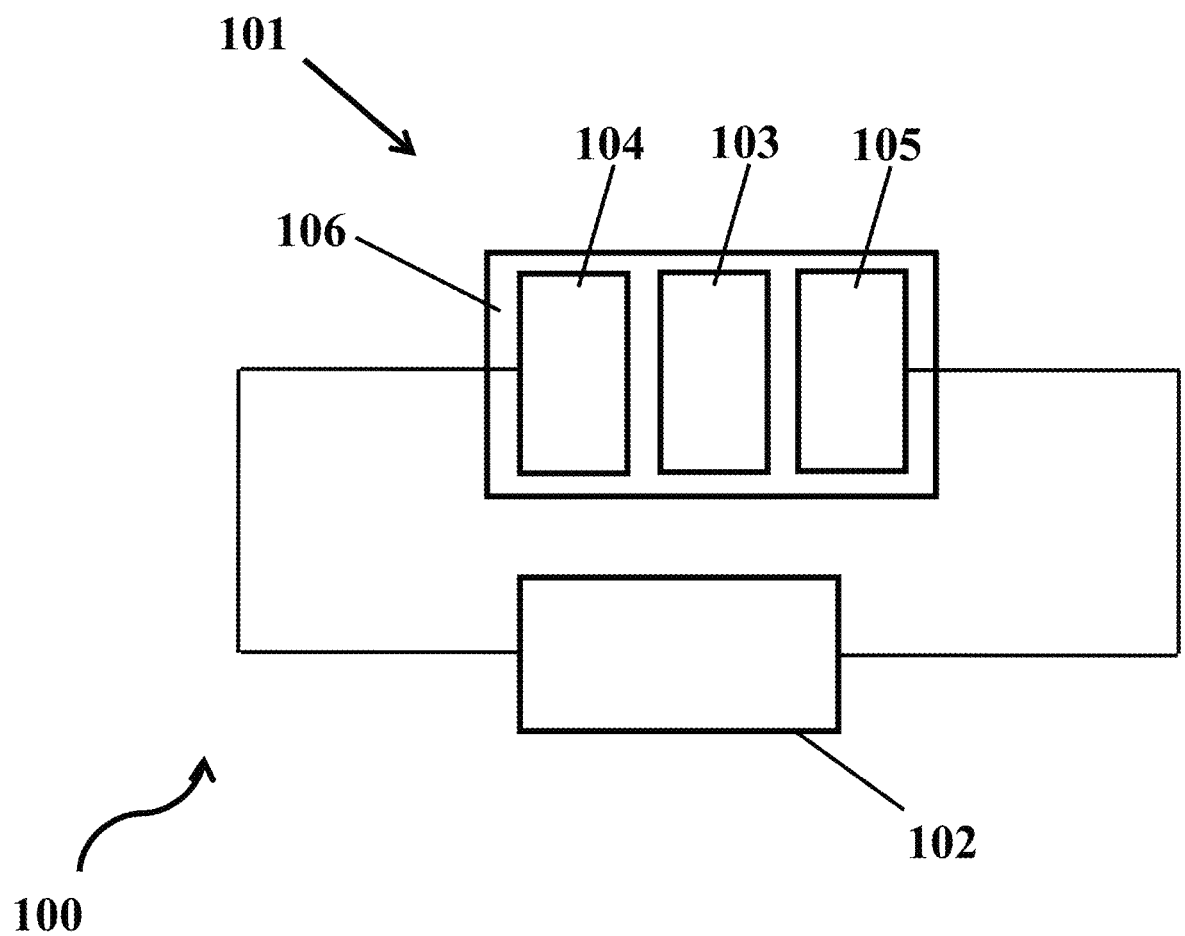
FIG. 1 illustrates a schematic of one example of an integrated biosensor used in conjunction with an electrochemical assay system, consistent with one or more exemplary embodiments of the present disclosure.

The following detailed description is presented to enable a person skilled in the art to make and use the methods and devices disclosed in exemplary embodiment of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Disclosed herein is an exemplary electrochemical method to detect the effect of an anticancer drug on cancer cells. The method can detect the anticancer drugs effect via measuring the cells ionic state changes that may be achieved via monitoring the anodic/cathodic current peaks of a plurality cell attached onto an array SiNW electrodes. The method may be considered as a new label-free electrochemical method to detect the electrochemical response of cancerous cells to a cancer treating drug.

As used herein, the "effect of an anticancer drug on cancer cells" refers to the cancer treating effect of the anticancer drug that induces a change in electrochemical properties of a biological cell that undergoes an anticancer drug treatment. Such effect is detectable through monitoring the shape and value of electrochemical responses of the treated cells, since the anticancer drug induces a change in the cells ionic state and resulting in an ionic non-equilibrium state to the cancer cells.

As used herein, the term "anticancer drug" refers to any compound or agent that can be used as therapeutic agent in cancer treatments that can perturb the ionic state of the cells.

In another aspect, the present disclosure describes an exemplary integrated electrical biosensor based on SiNWs (hereinafter "SiNW-based biosensor"). The biosensor may be used in conjunction with an electrochemical assay system instead of the system several separate electrodes.

In recent years, some generations of label free electrochemical biosensors have been developed and shed new lights in bio-analysis owing to their low cost, multiplexed detection capabilities, as well as ease of miniaturization without any additional biochemical processes. Engineering the bio-electrochemical sensing interface is crucial in such devices due to the impact of an accurate and stable response. Among various surface treatments used in interfacial modification, applying nanomaterials has presented various unique performances regarding their sizes and shapes. Great electrical conductivity, enlarged interactive surface area and well physiochemical interactions are some of the characteristics reported for many nanostructures ranged between metallic NPs to carbon nanotubes. Moreover, if the biocompatibility of nanostructures would be acceptable, sensing interfaces produced by nanostructures, would present new generation of label free biosensors for monitoring vital cells. SiNWs as a category of biocompatible nanomaterials having greatly controllable conductivity with good electron transport properties, enlarged electrochemically active area, good compatibility with silicon fabrication processes and well attachment of the cells to the outer wall of such nanostructures may be used herein to develop an effective electrochemical label free approach to monitor and detect the electrochemical assays of cancer cells during cancer treatments in a precise reliable way.

In an exemplary method, electrical responses from biological cells are measures using an exemplary biosensor. The integrated biosensor (hereinafter "SiNW-based biosensor") may include a working electrode, a counter electrode and a reference electrode, which may include arrays of SiNWs and are designed and fabricated in an integrated configuration on a single chip. The working electrode may be configured to contact to the biological cells and be an attachment site for the biological cells. The counter electrode may be configured to acquire the electrical response from the working electrode including the attached biological cells. The reference electrode may be configured to adjust a specific voltage around the working and the counter electrodes.

In some implementations, the electrical response may be an electrical current in a range of about 1 nA to about 100 µA and the specific voltage may be in a range of about −600 mV to about 600 mV.

In some implementations, the biosensor may be used in conjunction with an electrochemical assay device to measure an electrochemical response from the biological cells. For instance, the biosensor may be coupled with a cyclic voltammetric system or a potentiostat electrochemical assay system, in which the biosensor may be substituted instead of those systems electrodes to measure a cyclic voltammetry (CV) or a differential pulse voltammetry (DPV) electrochemical response.

FIG. 1 shows a schematic of an exemplary biosensor 101 used in conjunction with an electrochemical assay system 102, consistent with one or more exemplary embodiments of the present disclosure. The biosensor 101 may include three electrodes including a working electrode 103 including a first array of SiNWs, a counter electrode 104 including a second array of SiNWs and a reference electrode 105 including a third array of SiNWs that are integrated onto a chip 106. The chip 106 may be a silicon chip or a silicon wafer. The biosensor 101 may be substituted in an integrated configuration instead of three individually separated electrodes of an electrochemical assay system 102.

Figure 2A:
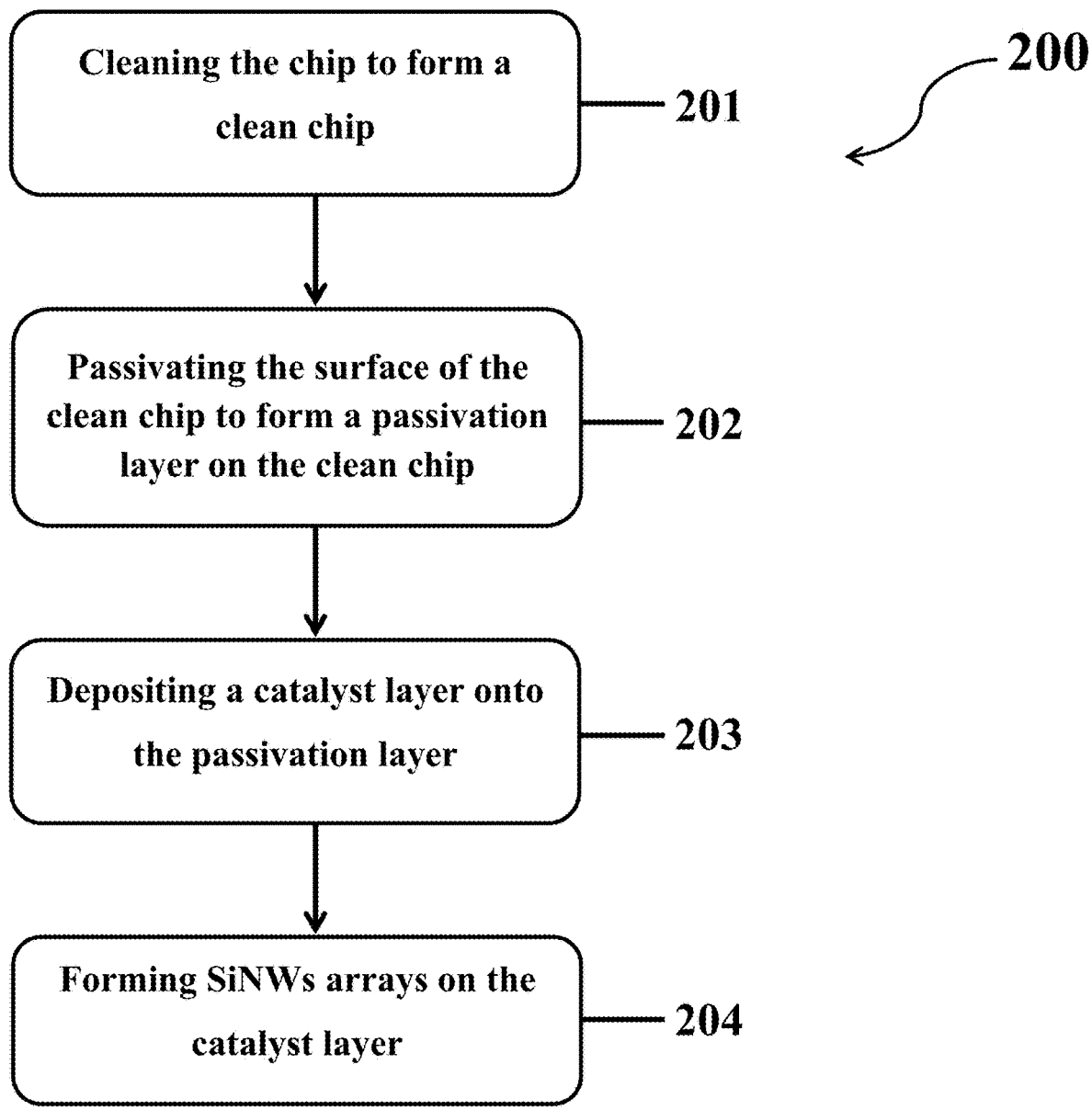
FIG. 2A illustrates an example of a method for design and fabricate three integrated SiNW arrays electrodes onto a chip, consistent with one or more exemplary embodiments of the present disclosure.

FIG. 2A shows an example of a method 200 to design and fabricate three arrays of SiNWs incorporated onto a silicon chip 106 forming three integrated electrodes of biosensor 101 on the chip, consistent with one or more exemplary embodiments of the present disclosure.

Referring to FIG. 2A, the first, the second and the third arrays of SiNWs may be designed and fabricated on a chip to form the biosensor 101 by a method including the steps of cleaning the chip to form a clean chip (step 201), passivating the surface of the clean chip to form a passivation layer on the clean chip (step 202), depositing a catalyst layer onto the passivation layer (step 203) and fourth, forming SiNWs arrays on the deposited catalyst layer (step 204).

Figure 2B:
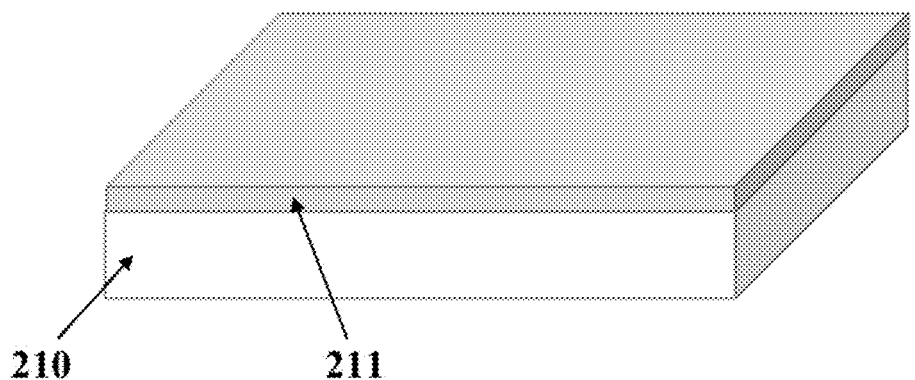
FIGS. 2B-2E illustrate exemplary steps of method for designing and fabricating three integrated SiNW arrays electrodes onto a chip, consistent with one or more exemplary embodiments of the present disclosure.

Exemplary illustration of the steps 201 to 204 are shown in FIGS. 2B-2E. In step 201, a silicon chip or a silicon wafer may be cleaned to remove impurities and form a clean chip. Subsequently, the clean chip obtained from step 201 may be passivated through step 202. In this step, a thin layer 211 of silicon dioxide ($SiO_2$) may be grown onto the surface of the clean chip 210 forming a passivation layer 211 on the clean chip as shown in FIG. 2B. The silicon dioxide ($SiO_2$) layer 211 may be grown on the clean chip 210 using a wet oxidation furnace. The passivation layer 211 may have a thickness in a range of about 100 nm to about 500 nm.

Figure 2C:
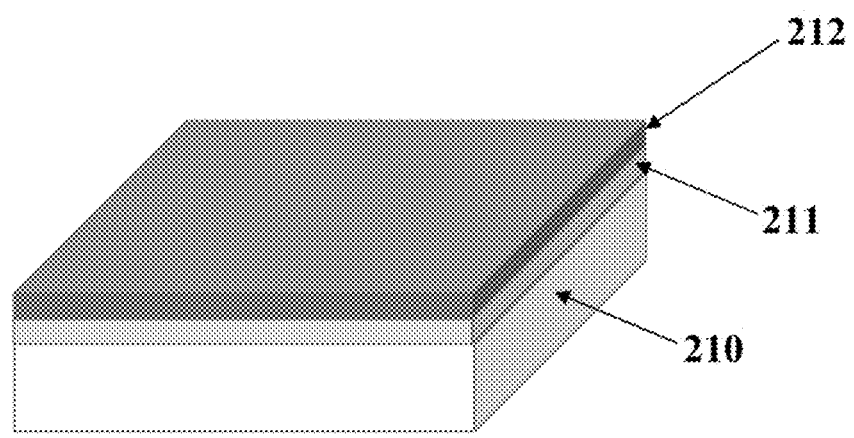

Moving on to step 203, a catalyst layer 212 may be deposited onto the passivation layer 211 as shown in FIG. 2C. The catalyst layer 212 may include a Gold (Au) layer with a thickness of about 5 nm. The catalyst layer 212 may be deposited onto the passivation layer 211 using a sputtering system and at a pressure of about 20 m Torr.

Moving on to step 204, the first, second and third SiNWs arrays may be formed on the deposited catalyst layer 212. The SiNWs arrays may be formed through a two-step process including: first, graining the catalyst layer to form three catalyst islands on the chip and second, growing three arrays of SiNWs onto the three catalyst islands.

Figure 2D:
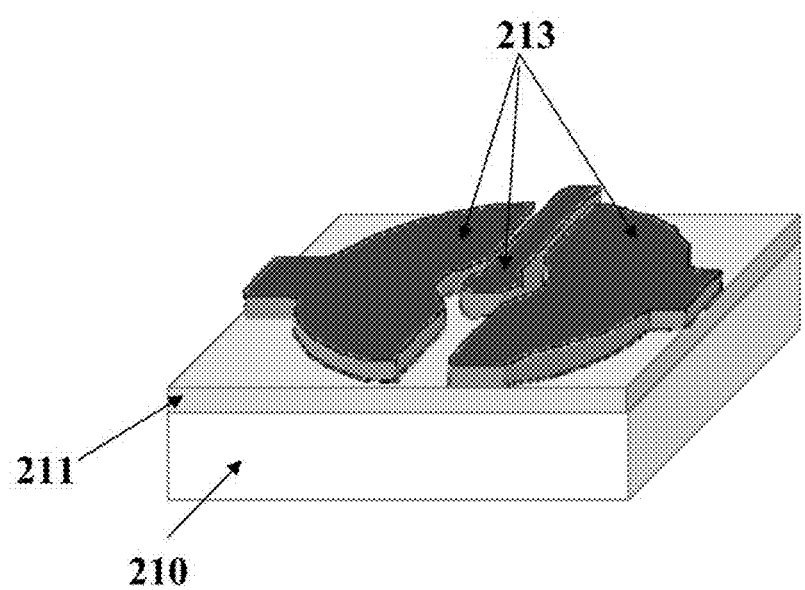
Figure 2E:
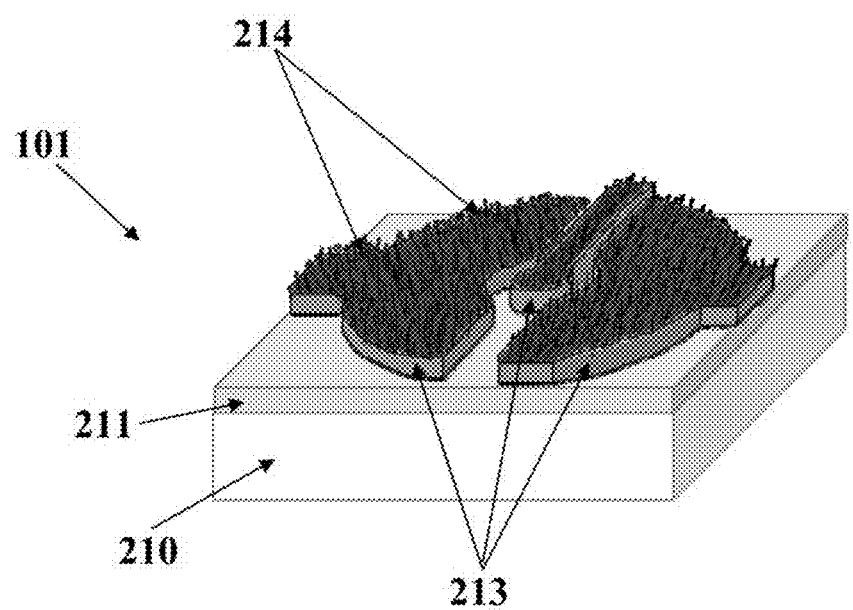

In some implementations, the SiNWs arrays may be formed on the catalyst layer using a low pressure chemical vapor deposition (LPCVD) system with a quartz tube chamber. Initially, the catalyst layer 212 may be grained to pattern the catalyst layer by architecture of the integrated work, counter and reference electrodes of biosensor 101 as shown in FIG. 2D. Correspondingly, three catalyst islands 213 may be formed on the chip. Graining the catalyst layer may be done via a thermal annealing process and in the presence of a carrier gas, for example Argon (Ar) gas. The graining of the catalyst layer may be done at a temperature range of about 450° C. to about 550° C. for a time interval about 30 minutes. Then, three arrays of SiNWs 214 may be grown onto the three catalyst islands as shown in FIG. 2E. The arrays of SiNWs may be grown onto the three catalyst islands 213 via a vapor-solid-liquid (VLS) process at a temperature of about 450° C. The VLS process may be done by assistance of a mixture of a silicon (Si) source (for example, silane ($SiH_4$)) and a carrier gas (for example, Argon (Ar). During the growth of SiNWs, Silicon nanowires may be formed on top of the three catalyst islands in their patterned regions.

Various exemplary methods and devices are disclosed, and examples may include a biosensor for measuring an electrical response from a biological sample and methods for fabricating the biosensor. The exemplary biosensor may be generally similar to exemplary biosensor 101. Exemplary biosensor 101 may have various implementations and configurations that may include various arrangements of three integrated electrodes, including working electrode, counter electrode and reference electrode. Exemplary biosensor 101 may include three integrated electrodes patterned on one chip and may be utilized for measuring electrochemical responses from biological samples, such as biological cells or cell lines.

Figure 2F:
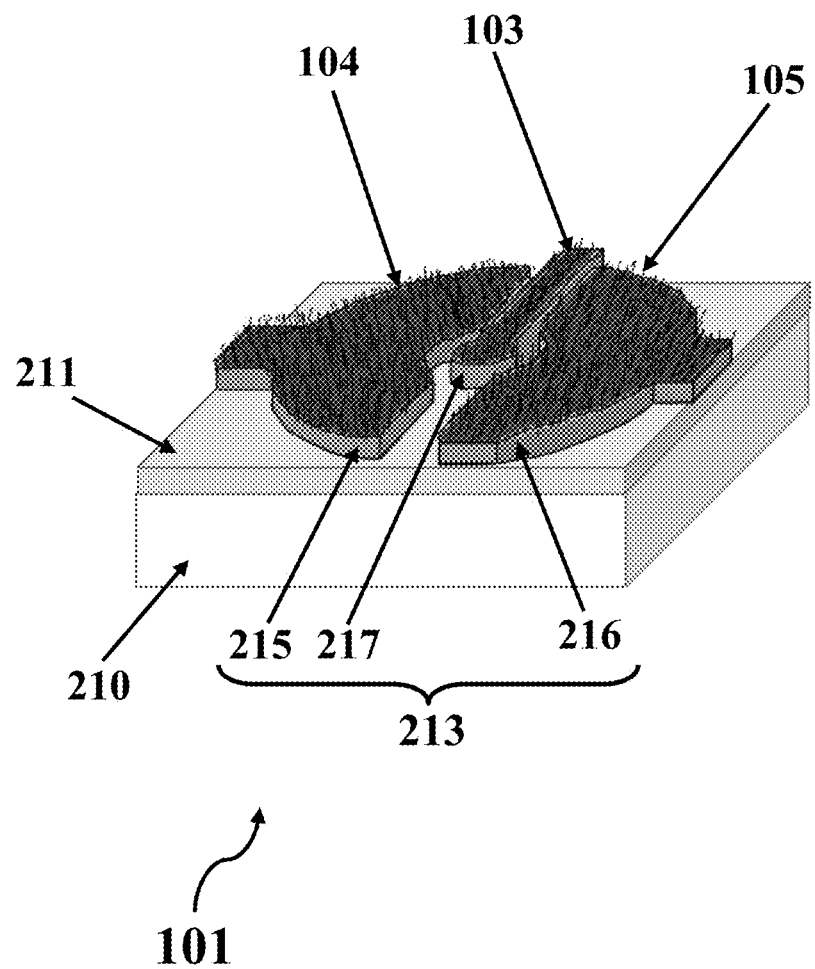
FIG. 2F illustrates a schematic view of an exemplary biosensor with a circular-patterned array of electrodes, consistent with one or more exemplary embodiments of the present disclosure.
Figure 2G:
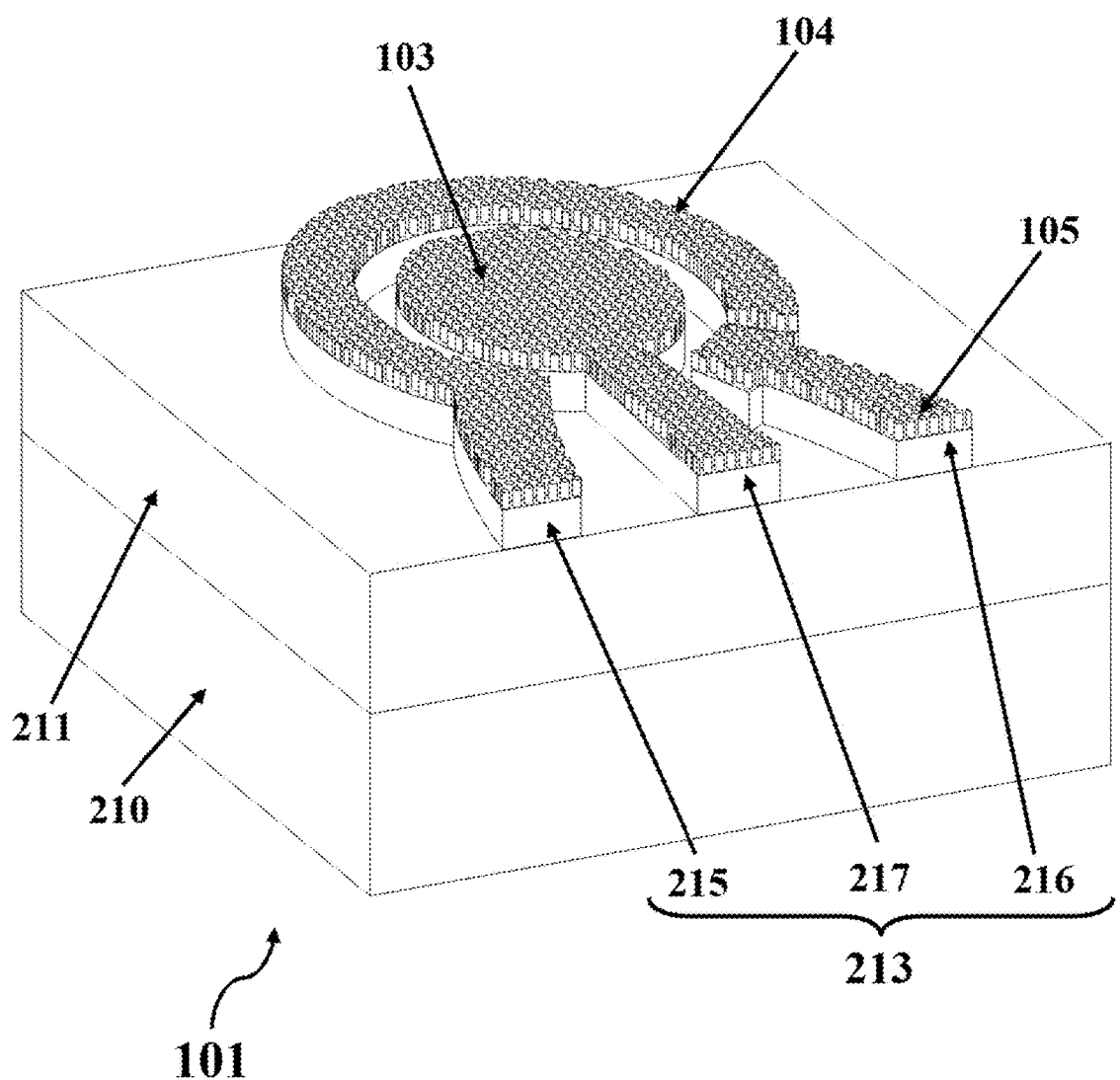
FIG. 2G illustrates a schematic view of an exemplary biosensor with another circular-patterned array of electrodes, consistent with one or more exemplary embodiments of the present disclosure.
Figure 2H:
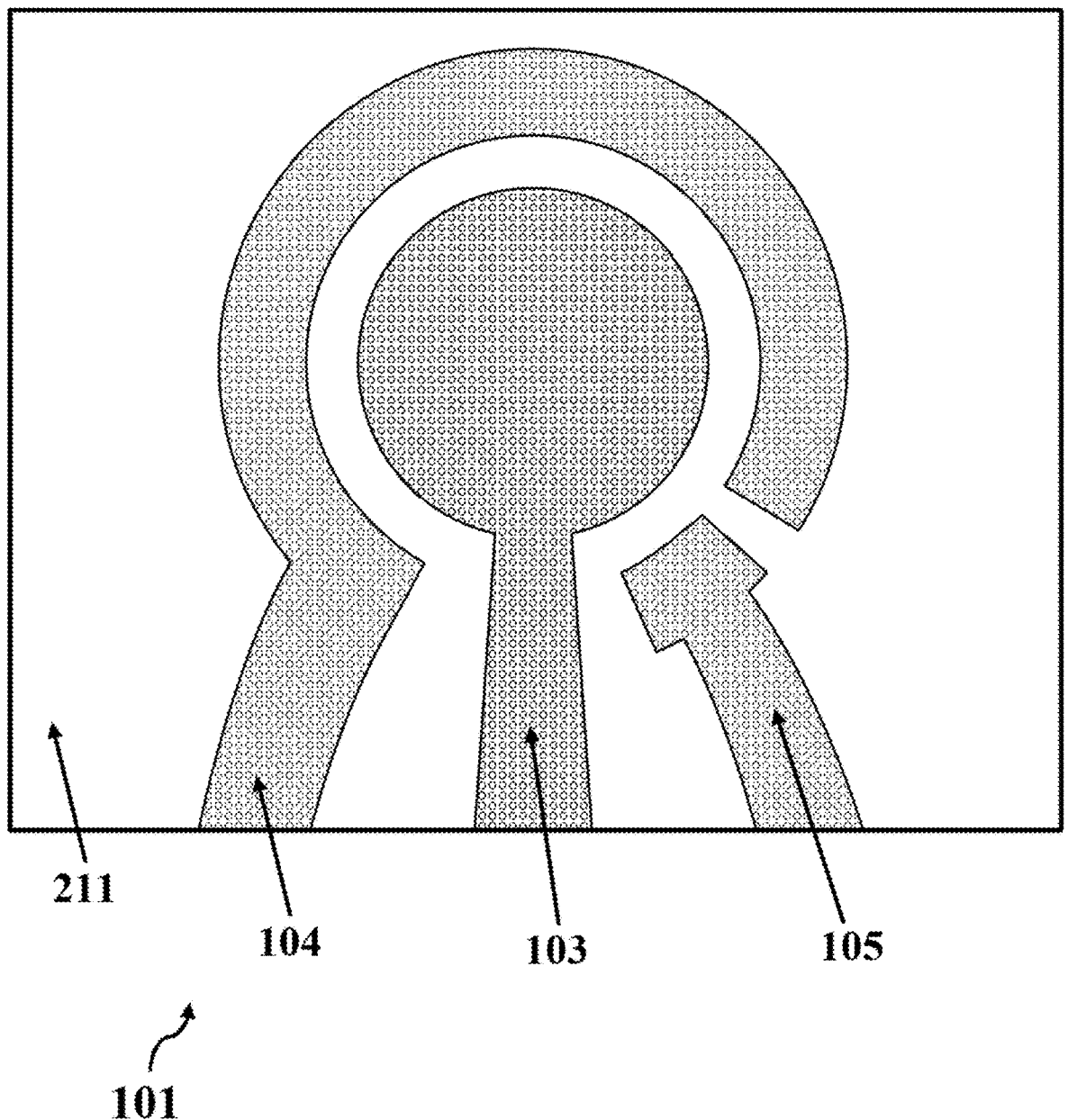
FIG. 2H illustrates a schematic top view of the exemplary biosensor with the circular-patterned array of electrodes, consistent with one or more exemplary embodiments of the present disclosure.
Figure 2I:
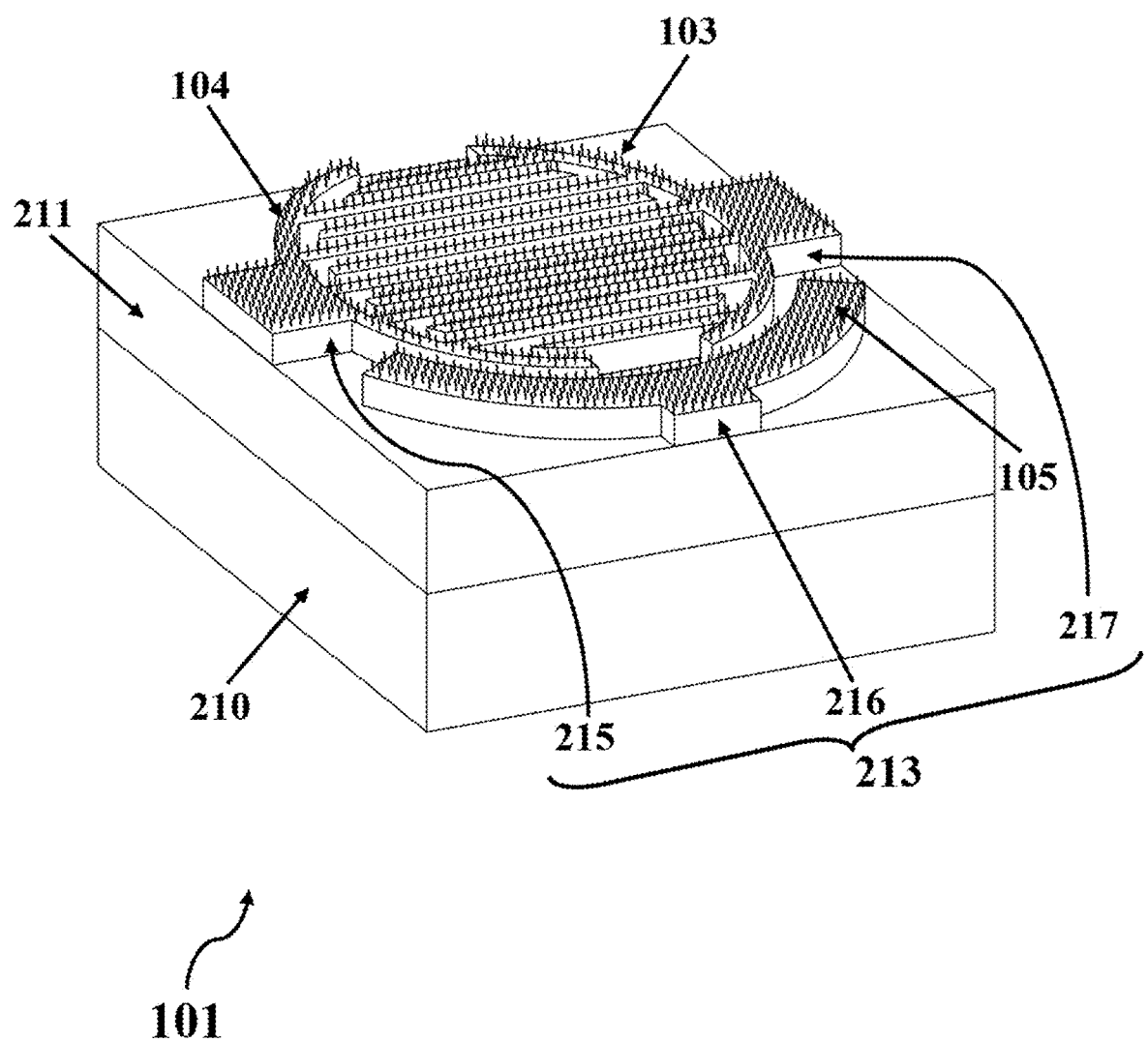
FIG. 2I illustrates a schematic view of an exemplary biosensor with an interdigital-patterned array of electrodes, consistent with one or more exemplary embodiments of the present disclosure.

FIGS. 2F-2G and 2I show three implementations of exemplary biosensor 101 for measuring an electrical response from a biological sample. Referring to FIGS. 2F, 2G and 2I, exemplary biosensor 101 may include substrate 210, passivation layer 211, patterned catalyst layer 213, and three integrated electrodes 103, 104, and 105 grown on patterned catalyst layer 213. In an exemplary embodiment, patterned catalyst layer 213 may include catalyst islands 217, 215, and 216 respective to three integrated electrodes 103, 104, and 105. In an exemplary embodiment, catalyst island 217 may include a catalyst layer 217 that may be configured to grow working electrode 103 thereon. In an exemplary embodiment, catalyst island 215 may include a catalyst layer 215 that may be configured to grow counter electrode 104 thereon. In an exemplary embodiment, catalyst island 216 may include a catalyst layer 216 that may be configured to grow reference electrode 105 thereon.

In an exemplary embodiment, exemplary substrate 210 may include at least one of a silicon chip and a silicon wafer.

In an exemplary embodiment, exemplary passivation layer 211 may include an electrical passivating layer grown on a surface of exemplary substrate 210. In one example, exemplary passivation layer 211 may include a layer of silicon dioxide ($SiO_2$) with a thickness in a range between about 100 nm and about 500 nm. In an exemplary implementation, exemplary passivation layer 211 maybe grown on the surface of exemplary substrate 210 using a wet oxidation furnace. Exemplary passivation layer 211 maybe grown on the surface of exemplary substrate 210 in order to electrically passivate (isolate) the surface of exemplary substrate 210.

In an exemplary embodiment, exemplary patterned catalyst layer 213 may include three catalyst islands 213 that may include three respective catalyst substrates for growing three integrated electrodes 103, 104 and 105 thereon. In an exemplary embodiment, exemplary patterned catalyst layer 213 may include a patterned catalyst layer deposited on exemplary passivation layer 211. In an exemplary embodiment, exemplary patterned catalyst layer 213 may include a layer of a catalyst for growing a plurality of nanostructures thereon. The nanostructures may be configured to include three integrated electrodes 103, 104 and 105. In an exemplary embodiment, the plurality of nanostructures may include at least one of silicon nanowires (SiNWs), silicon nanograss, carbon nanotubes (CNTs), and combinations thereof.

In an exemplary embodiment, exemplary patterned catalyst layer 213 may include a layer of at least one of nickel (Ni), gold (Au), iron (Fe), and combinations thereof, which may be deposited and patterned on exemplary passivation layer 211. In an exemplary embodiment, exemplary patterned catalyst layer 213 may include a layer of a catalyst with a thickness of less than about 10 nm for growing electrically conductive biocompatible nanostructures thereon.

In an exemplary implementation, exemplary patterned catalyst layer 213 may be formed on exemplary passivation layer 211 via a process that may include depositing a layer of a catalyst on exemplary passivation layer 211 and patterning the deposited layer of the catalyst on exemplary passivation layer 211. In one exemplary scenario, depositing the layer of the catalyst on exemplary passivation layer 211 may include coating the layer of the catalyst on exemplary passivation layer 211 using a sputtering system. In another exemplary scenario, depositing the layer of the catalyst on exemplary passivation layer 211 may include coating the layer of the catalyst on exemplary passivation layer 211 by utilizing an E-beam evaporation system at a temperature of about 120° C. with depositing rate of about 0.1 Angstroms/s. In one example, patterning the deposited layer of the catalyst may include forming three separated catalyst islands 213, for example, by using a photolithography technique. Exemplary three separated catalyst islands 213 may include three growth sites for growing three integrated electrodes 103, 104, and 105 thereon that may include three arrays of electrically conductive biocompatible nanostructures.

In an exemplary embodiment, three integrated electrodes 103, 104, and 105 may include exemplary working electrode 103, exemplary counter electrode 104, and exemplary reference electrode 105. In an exemplary embodiment, three integrated electrodes 103, 104, and 105 may include three arrays of electrically conductive biocompatible nanostructures grown on exemplary patterned catalyst layer 213. In another exemplary embodiment, only working electrode 103 may include an array of electrically conductive biocompatible nanostructures. In such cases, exemplary electrodes 104 and 105 may only include two respective catalyst islands of three separated catalyst islands 213. Exemplary working electrode 103 may be grown on a respective catalyst layer island of exemplary patterned catalyst layer 213 that may be configured to be a target site for exemplary working electrode 103.

In an exemplary embodiment, exemplary working electrode 103 may include a first array of electrically conductive biocompatible nanostructures 103 that may be configured to be an attachment site for a biological sample. In an exemplary embodiment, exemplary counter electrode 104 may include a second array of electrically conductive biocompatible nanostructures 104 that may be configured to acquire, capture, or receive an electrical response from exemplary working electrode 103. In an exemplary embodiment, exemplary reference electrode 105 may include a third array of electrically conductive biocompatible nanostructures 105 that may be configured to adjust a specific voltage around exemplary working electrode 103 and exemplary counter electrode 104.

In one exemplary scenario, electrochemical assay system 102 may include a potentioastat device. Three integrated electrodes 103, 104, and 105 may be connected to the potentioastat device. An exact electrical voltage waveform with an amount of about −0.8 V to 0.8 V at a scan rate of about 100 mv/s may be adjusted utilizing the potentioastat device and may be applied to exemplary reference electrode 105 from the potentioastat device. Additionally, exemplary counter electrode 104 may be configured to collect or acquire an electrical current which may flows between exemplary counter electrode 104 and exemplary working electrode 103 in response to the applied adjusted voltage to exemplary reference electrode 105.

In an exemplary embodiment, the electrically conductive biocompatible nanostructures may include at least one of silicon nanowires (SiNWs), silicon nanograss, carbon nanotubes (CNTs), and combinations thereof. In an exemplary embodiment, the SiNWs may include a plurality of SiNWs with a width of less than about 80 nm and a length of less than about 50 µm. In an exemplary embodiment, the SiNWs may include a plurality of SiNWs with a width between about 10 nm and about 80 nm and a length of between about 1 µm and about 50 µm. In an exemplary embodiment, the CNTs may include a plurality of vertically aligned multi-walled carbon nanotubes (VAMWCNTs). In an exemplary embodiment, the CNTs may include CNTs with a length of between about 0.5 µm and about 10 µm and a diameter of between about 20 nm and about 100 nm. In an exemplary embodiment, the CNTs may include CNTs with a length of less than about 100 nm.

In an exemplary embodiment, the SiNWs may be formed on catalyst islands 213; thereby, forming exemplary three integrated electrodes 103, 104, and 105. In an exemplary embodiment, the SiNWs may be formed on catalyst islands 213 using a low pressure chemical vapor deposition (LPCVD) system with a quartz tube chamber. The SiNWs may be formed on catalyst islands 213 via a process, including graining catalyst islands 213, and growing three arrays of SiNWs on the grained catalyst islands 213. Graining catalyst islands 213 may be done via a thermal annealing process and in the presence of a carrier gas, for example Argon (Ar) gas. The graining catalyst islands 213 may be done at a temperature range of about 450° C. to about 550° C. for a time interval about 30 minutes. Then, three arrays of SiNWs may be grown onto the grained catalyst islands 213. The arrays of SiNWs may be grown onto the catalyst islands 213 via a vapor-solid-liquid (VLS) process at a temperature of about 450° C. The VLS process may be done by assistance of a mixture of a silicon (Si) source (for example, silane ($SiH_4$)) and a carrier gas (for example, Argon (Ar). During the growth of SiNWs, Silicon nanowires may be formed on top of the three catalyst islands 213 in their patterned regions.

In an exemplary embodiment, the CNTs may be formed on catalyst islands 213; thereby, forming exemplary three integrated electrodes 103, 104, and 105. In an exemplary embodiment, three arrays of VAMWCNTs may be grown on catalyst islands 213 using a direct current plasma enhanced chemical vapor deposition (DC-PECVD) system. The exemplary growth process of VAMWCNTs may include three steps of: annealing at a temperature of about 680° C. in an $H_2$ environment with a flow rate of about 35 standard cubic centimeters per minute (sccm) for about 30 minutes; graining, including plasma hydrogenation of surface for about 5 minutes with the intensity of about 5.5 W.cm$^{-2}$ that may result in the catalyst layer 213 graining and formation of Ni nano-sized islands, and growth of VAMWCNTs by introducing a plasma of $C_2H_2$ and $H_2$ mixture with flow rates of about 5 sccm and about 35 sccm to the chamber for about 15 minutes. Each of the VAMWCNTs may have a length between about 0.5 μm and about 5 μm and a diameter between about 20 nm and about 100 nm.

In an exemplary embodiment, exemplary patterned catalyst layer 213 may include three separated catalyst islands 215, 216, and 217 that may be integrated on exemplary passivation layer 211. Exemplary patterned catalyst layer 213 may include various patterns; thereby, forming various patterns and configurations for exemplary electrodes 103, 104, and 105. In an exemplary embodiment, exemplary patterned catalyst layer 213 may include one of a circular-patterned catalyst layer and an interdigital-patterned catalyst layer.

As described above, FIGS. 2E and 2F show a schematic view of exemplary biosensor 101 with a circular-patterned array of electrodes, consistent with one or more exemplary embodiments of the present disclosure. Referring to FIG. 2F, exemplary patterned catalyst layer 213 may include a circular-patterned catalyst layer. In an exemplary embodiment, exemplary circular-patterned catalyst layer 213 may include a first semi-circular layer of catalyst 215, a second semi-circular layer of catalyst 216, and a circular layer of catalyst 217. Exemplary first semi-circular layer of catalyst 215, second semi-circular layer of catalyst 216, and circular layer of catalyst 217 may be deposited and patterned on exemplary passivation layer 211.

In an exemplary embodiment, exemplary first semi-circular layer of catalyst 215 may be configured to grow the second array of electrically conductive biocompatible nanostructures thereon; thereby, forming exemplary counter electrode 104. Exemplary second semi-circular layer of catalyst 216 may be configured to grow the third array of electrically conductive biocompatible nanostructures thereon; thereby, forming exemplary reference electrode 105. Exemplary circular layer of catalyst 217 may be configured to grow the first array of electrically conductive biocompatible nanostructures thereon; thereby, forming exemplary working electrode 103.

FIG. 2G shows a schematic view of exemplary biosensor 101 with another circular-patterned array of electrodes, consistent with one or more exemplary embodiments of the present disclosure. Additionally, FIG. 2H shows a schematic top view of exemplary biosensor 101 with the circular-patterned array of electrodes in connection with FIG. 2G, consistent with one or more exemplary embodiments of the present disclosure. Referring to FIGS. 2G-2H, exemplary patterned catalyst layer 213 may include another circular-patterned catalyst layer in addition to that shown in FIG. 2F. In an exemplary embodiment, exemplary circular-patterned catalyst layer 213 may include a circular layer of catalyst 217, a partially annular layer of catalyst of catalyst 215, and a reference-site layer of catalyst 216. Exemplary circular layer of catalyst 217, partially annular layer of catalyst of catalyst 215, and reference-site layer of catalyst 216 may be deposited and patterned on exemplary passivation layer 211. In an exemplary embodiment, partially annular layer of catalyst of catalyst 215 may be deposited and patterned on exemplary passivation layer 211 around exemplary circular layer of catalyst 217. In an exemplary embodiment, reference-site layer of catalyst 216 may be deposited and patterned on exemplary passivation layer 211 adjacent to exemplary circular layer of catalyst 217 and the partially annular layer of catalyst 215.

In an exemplary embodiment, exemplary partially annular layer of catalyst of catalyst 215 may be configured to grow the second array of electrically conductive biocompatible nanostructures thereon; thereby, forming exemplary counter electrode 104. Exemplary reference-site layer of catalyst 216 may be configured to grow the third array of electrically conductive biocompatible nanostructures thereon; thereby, forming exemplary reference electrode 105. Exemplary circular layer of catalyst 217 may be configured to grow the first array of electrically conductive biocompatible nanostructures thereon; thereby, forming exemplary working electrode 103.

In an exemplary implementation, such circular-patterned array of electrodes may lead to a uniform and dense distribution of electrical field around exemplary working electrode 103; thereby, allowing for high accurate electrical measurements using exemplary electrochemical biosensor 101 with exemplary circular-patterned array of electrodes.

Figure 2J:
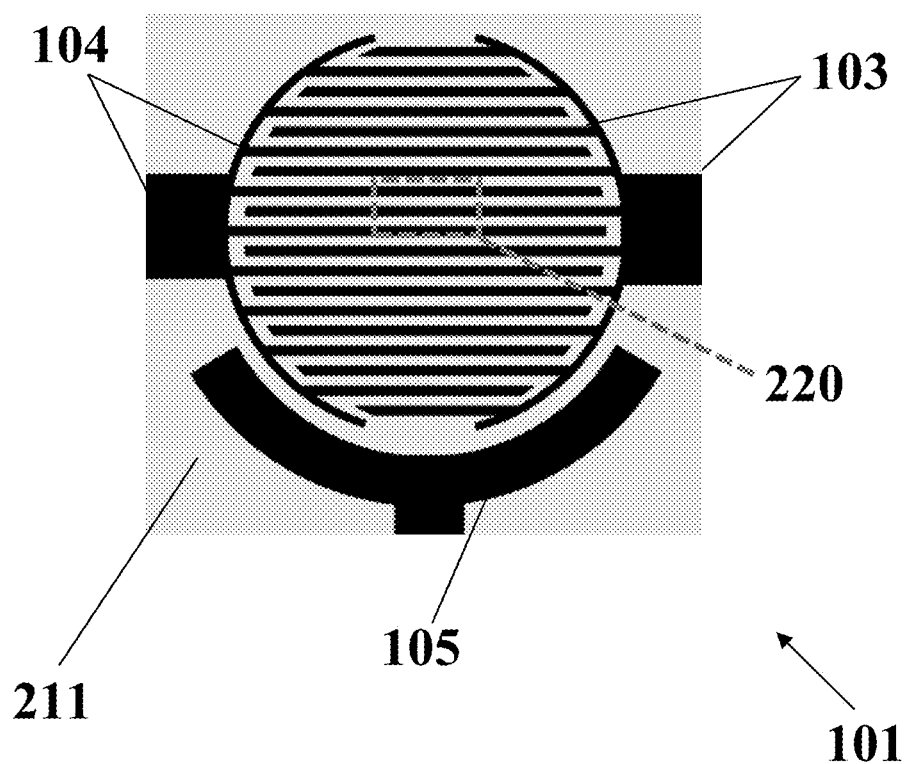
FIG. 2J illustrates a schematic top view of the exemplary biosensor with the interdigital-patterned array of electrodes, consistent with one or more exemplary embodiments of the present disclosure.

FIG. 2I shows a schematic view of exemplary biosensor 101 with an interdigital-patterned array of electrodes, consistent with one or more exemplary embodiments of the present disclosure. Additionally, FIG. 2J shows a schematic top view of exemplary biosensor 101 with the interdigital-patterned array of electrodes in connection with FIG. 2I, consistent with one or more exemplary embodiments of the present disclosure. Referring to FIGS. 2I-2J, exemplary interdigital-patterned catalyst layer 213 may include a first teeth-shaped array of catalyst layer 217, a second teeth-shaped array of catalyst layer 215, and a singular layer of catalyst 216. Exemplary first teeth-shaped array of catalyst layer 217, second teeth-shaped array of catalyst layer 215, and singular layer of catalyst 216 may be deposited and patterned on exemplary passivation layer 211. In an exemplary embodiment, singular layer of catalyst 216 may be placed adjacent to the first teeth-shaped array of catalyst layer 217 and the second teeth-shaped array of catalyst layer 215.

In an exemplary embodiment, exemplary first teeth-shaped array of catalyst layer 217 may be configured to grow the first array of electrically conductive biocompatible nanostructures thereon; thereby, forming exemplary working electrode 103. Exemplary second teeth-shaped array of catalyst layer 215 may be configured to grow the second array of electrically conductive biocompatible nanostructures thereon; thereby, forming exemplary counter electrode 104. Exemplary singular layer of catalyst 216 may be configured to grow the third array of electrically conductive biocompatible nanostructures thereon; thereby, forming exemplary reference electrode 105.

In an exemplary embodiment, the first teeth-shaped array of catalyst layer 217 and the second teeth-shaped array of catalyst layer 215 may be placed inside each other. In an exemplary embodiment, each of the first teeth-shaped array of catalyst layer 217 and the second teeth-shaped array of catalyst layer 215 may include a comb-patterned array of catalyst; thereby, forming a comb-patterned (interdigital-patterned) array of exemplary integrated electrodes 103, 104 and 105. Therefore, exemplary working electrode 103 and exemplary counter electrode 104 may include two comb-patterned (interdigital-patterned) arrays with two teeth-shaped arrays which may be placed inside each other.

In an exemplary implementation, the interdigital or comb-shaped pattern of electrodes may lead to a uniform and dense distribution of electrical field around exemplary working electrode 103; thereby, allowing for high accurate electrical measurements using exemplary electrochemical biosensor 101 with exemplary interdigital-patterned array of electrodes. The interdigital or comb-shaped pattern of electrodes may allow for utilizing arrays of electrically conductive biocompatible nanostructures in more dimensions and more effective surface area. In an exemplary embodiment, more teeth may be preferred to obtain a more intensified and uniform electrical field around exemplary working electrode 103.

In an exemplary embodiment, each of the first teeth-shaped array of catalyst layer 217 and the second teeth-shaped array of catalyst layer 215 may include an array of teeth-shaped catalyst layer with a distance between about 5 µm and about 200 µm for each two teeth patterned next to each other. In an exemplary embodiment, each tooth of the first teeth-shaped array of catalyst layer 217 and the second teeth-shaped array of catalyst layer 215 may include a tooth with a width between about 5 µm and about 200 µm. In an exemplary embodiment, each tooth of the first teeth-shaped array of catalyst layer 217 may be placed next to at least one tooth of the second teeth-shaped array of catalyst layer 215. In an exemplary embodiment, a distance between each tooth of the first teeth-shaped array of catalyst layer 217 and an adjacent tooth of the second teeth-shaped array of catalyst layer 215 may be the same as the width of each teeth.

Figure 2K:
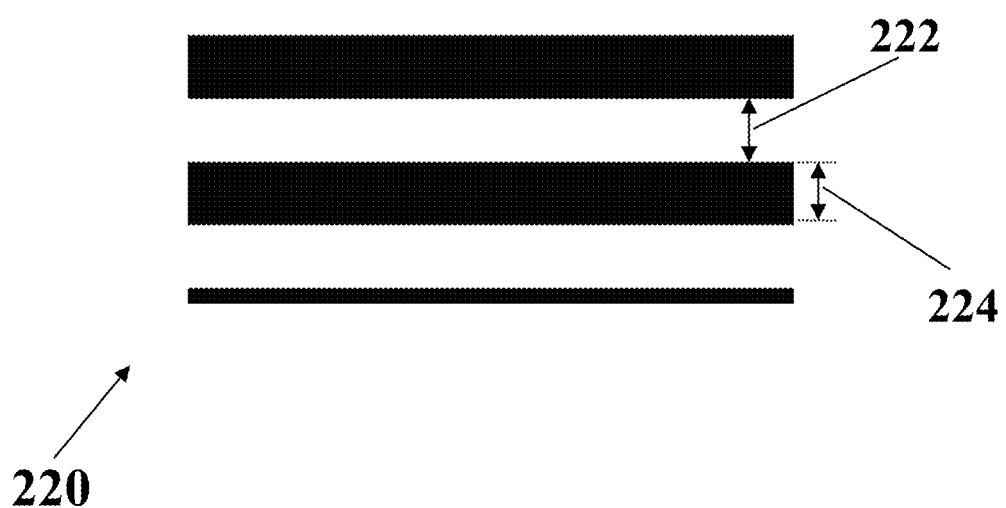
FIG. 2K illustrates a magnified schematic view of a portion of interdigital-patterned working electrode and counter electrode, consistent with one or more exemplary embodiments of the present disclosure.

FIG. 2K shows a magnified schematic view of a portion 220 of exemplary interdigital-patterned working electrode 103 and counter electrode 104, consistent with one or more exemplary embodiments of the present disclosure. In an exemplary embodiment, distance 222 between each two teeth of exemplary working electrode 103 and exemplary counter electrode 104 may be in a range of between about 5 µm and about 200 µm. In an exemplary embodiment, a width 224 of each tooth of exemplary working electrode 103 or counter electrode 104 may be in a range of between about 5 µm and about 200 µm. In an exemplary embodiment, distance 222 between each two teeth of the working electrode 103 and counter electrode 104, and width 224 of each tooth of exemplary working electrode 103 or counter electrode 104 may have the same length, which may be in a range of between about 5 µm and about 200 µm. In an exemplary embodiment, the distance 222 between each two teeth of the working electrode 103 and counter electrode 104 may be in a range of between about 5 µm and about 50 µm. In an exemplary embodiment, a width 224 of each tooth of exemplary working electrode 103 or counter electrode 104 may be in a range of between about 5 µm and about 50 µm. In an exemplary embodiment, distance 222 between each two teeth of the working electrode 103 and counter electrode 104, and width 224 of each tooth of exemplary working electrode 103 or counter electrode 104 may have the same length, which may be in a range of between about 5 µm and about 50 µm.

It should be understood that the biosensor 101 designed and fabricated according to one or more embodiments of the present disclosure may be used to electrochemically monitor the effect of any external biochemical stimulation on the vitality and function of biological cells by tracking any ionic non-equilibrium induced in the biosensor. For instance, the anticancer drugs are one of the clinically applicable biochemical stimulators of the cancer cells.

Exemplary biosensors as manufactured with respect to methods described in connection with FIGS. 1 and 2A-2E may be utilized to detect the effect of an anticancer drug on cancer cells.

Figure 3:
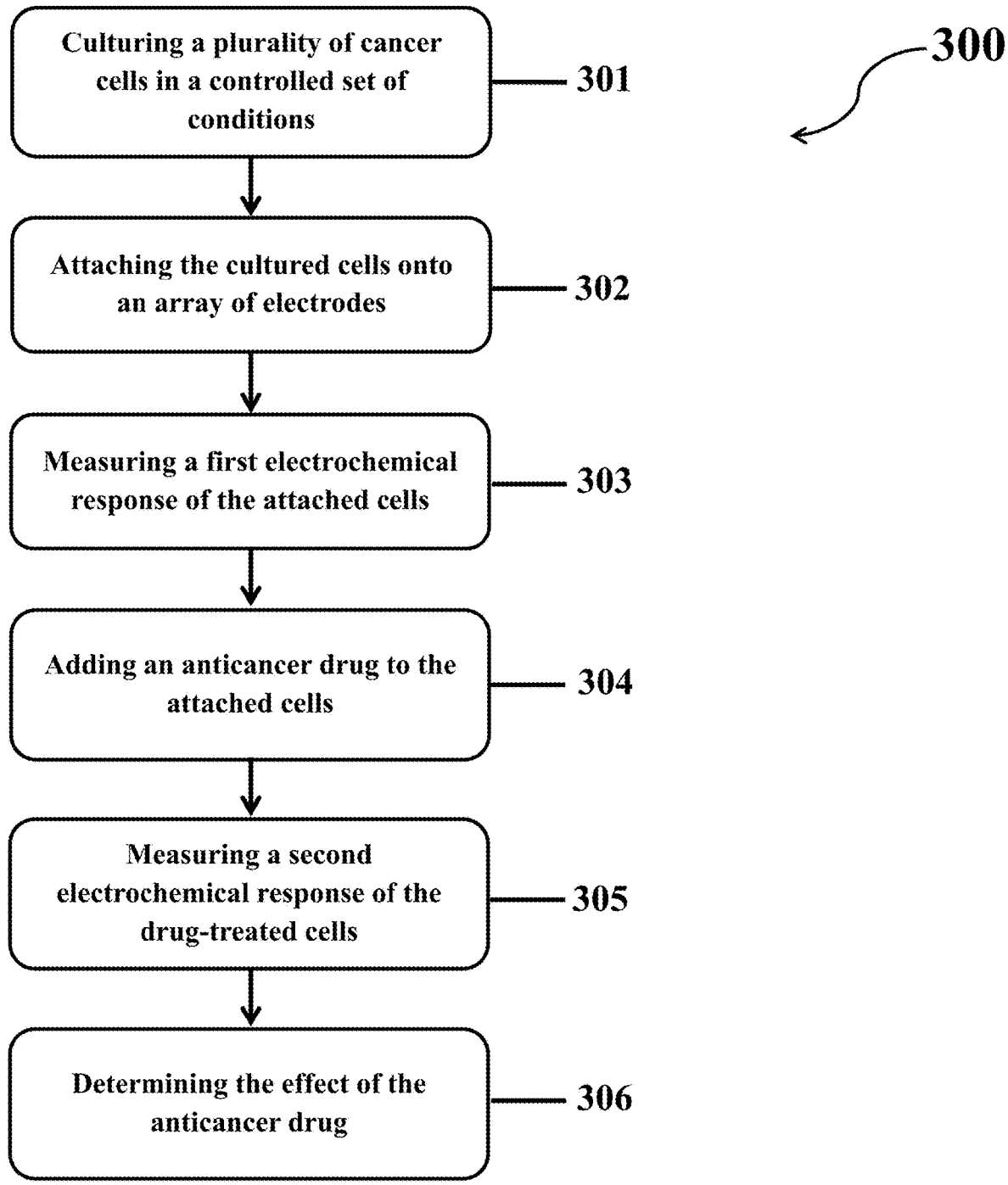
FIG. 3 illustrates an example of a method for detecting the electrochemical effect of an anticancer drug on cancer cells, consistent with one or more exemplary embodiments of the present disclosure.

For Example, FIG. 3 shows an exemplary method 300 for detecting the effect of an anticancer drug on cancer cells, consistent with one or more exemplary embodiments of the present disclosure. Method 300 may include the steps of culturing a plurality of cancer cells in a set of controlled conditions to form a plurality of cultured cells (step 301), attaching the cultured cells onto an array of electrodes (step 302), measuring a first electrochemical response of the attached cells onto the array of electrodes (step 303), adding an anticancer drug to the attached cells onto the array of electrodes to form drug-treated cells (step 304), measuring a second electrochemical response of the drug-treated cells (step 305), and determining the effect of the anticancer drug on the cancer cells based on a comparison of the first and the second electrochemical responses (step 306).

In step 301, a plurality of cancer cells may be cultured forming a plurality of cultured cells onto a for example, a glass substrate. The cells may be cultured in a set of controlled conditions including maintaining cancer cells in a $CO_2$ (about 5% $CO_2$, 95% clean air) incubator at a temperature of about 37° C. and in a culture medium, for example, a Roswell Park Memorial Institute-1640 (RPMI-1640) medium. The culture medium may be supplemented with a serum-supplement, for example, Fetal bovine serum (FBS) including Fetal bovine with an amount of about 5% and the culture medium may be further supplemented with an antibiotic in a specific amount, for example, penicillin/streptomycin antibiotic with an amount of about 1%. The fresh medium may be replaced every other day. Then, the cultured cells may be washed with a buffer solution, for example, a Phosphate-buffered saline (PBS) solution to remove the remained culture medium and supplements from the cultured cells.

In some exemplary implementations, the cancer cells may be epithelial cancer cells, for example breast cancer cells and the anticancer drug may be a drug that can induce an ionic non-equilibrium state into the cancer cells. The anticancer drug may be for example, an antitubulin drug that may perturb cells growth cycle or destroy the cells cytoskeleton, causing a change in ionic state of the cancer cells, that effects on the electrochemical characteristics and responses of the cells.

Referring to step 302, the cultured cells may be attached onto an array of electrodes. Attaching the cultured cells onto an array of electrodes may include detaching the cultured cells from the cell culture medium, dropping the detached cells on the array of electrodes, and maintaining the array of electrodes at specific conditions to obtain an attachment between the dropped cultured cells and the electrodes. The array of electrodes may include, for example, an array of silicon nanowires (SiNWs) designed and fabricated to use in electrochemical measurements, as described with respect to exemplary embodiments of the present disclosure with respect to FIGS. 1 and 2A-2E.

Accordingly, the cultured and washed cells obtained from step 301 may be trypsinized by assistance of adding a solution including trypsin and EDTA to the cultured cells in order to detach the cultured cells from the substrate. To minimize the effect of trypsinization, the procedure may be done in less than about 4 minutes at a room temperature in a range of about 20° C. to 22° C. The obtained solution having the cultured cells may be centrifuged to discard the trypsinizing solution from the detached cells. Subsequently, the detached cells may be dropped onto an array of electrodes, including for example, an array of SiNW electrodes. Then, the array of electrodes including the dropped cells may be maintained at specific conditions, for example, in an incubator at a temperature of about 37° C. and for about 4 hours to achieve an attachment between the dropped cultured cells and the electrodes.

Moving on to step 303, a first electrochemical response of the attached cells onto the array of electrodes may be measured as a control or a base value for further comparisons with a second electrochemical response of a same type that may be measured after adding an anticancer drug to the attached cells as will be described further in greater details with reference to step 305.

In step 304, an anticancer drug may be used to form anticancer drug-treated cells. Forming the exemplary anticancer drug-treated cells may include adding anticancer drug in a specific amount to the cultured cells attached onto the array of electrodes and maintaining the array of electrodes including the attached cultured cells with the added anticancer drug at specific conditions to form drug-treated cells onto the electrodes. The anticancer drug may be added in a concentration of about 0.1 nano-mole per liter to about 20 nano-mole per liter. To achieve a drug treatment affected by the added anticancer onto the attached cells onto the electrodes, the array of electrodes including the attached cultured cells with the added anticancer drug may be maintained in an incubator for at least 2 hours that may be taken long to about 12 hours or more.

Moving on to step 305, a second electrochemical response of the anticancer drug-treated cells formed during step 304 may be measured to compare with the control value measured in step 303. Moving, on stop step 306, the effect of the anticancer drug on the cancer cells may be determined based on a comparison of the first and the second electrochemical responses. Specifically, it may be determined that the anticancer drug is effective if there are changes and differences between the first and the second electrochemical responses. If it is determined that there are no changes between the first and the second electrochemical responses, it may be determined that the anticancer drug is not effective. In some exemplary cases, the anticancer drug affects the ionic equilibrium of the cells, so the treated cancer cells start to remedy the non-equilibrium state. For example, when the drug-treated cancer cells undergo a reduction reaction of cytochrome C within the cell due to an electrochemical effect of the drug, there is an accumulation of positive charge within the cells. So a change in electrical current may be formed in the solution including the drug-treated cells on the electrodes in comparison with the initial electrical current within the solution. The initial electrical current may be considered as the first electrochemical response and the second electrochemical response may include the second electrical current after drug treatment. The amount of change in electrical current due to the drug treatment may depend on the drug concentration, time of treatment, cells concentration, etc. In some examples, the first electrochemical response may include smoother curves of electrical current versus applied voltages with smaller amounts of electrical currents. After treating the cells with the anticancer drug, if the anticancer drug affect the cells, the second electrochemical response may include curves of electrical current versus applied voltages having sharp peaks in comparison with the first electrochemical response and may show larger amounts or values of electrical current, for example about 1000 times greater than those for the first electrochemical response.

Referring again to steps 303 and 304, the first and the second electrochemical responses may be for example, a cyclic voltammetry (CV) assay or a differential pulse voltammetry (DPV) response. The first and the second electrochemical responses may be measured by assistance of an integrated electrical biosensor that can be used in couple with an electrochemical assay system. The integrated electrical biosensor may be substituted instead of the electrochemical assay system electrodes. The electrochemical assay system may be a cyclic voltammetric system or a potentiostat system.

In some implementations, the integrated electrical biosensor may include a working electrode, a counter electrode and a reference electrode designed and fabricated on a single chip, consistent with one or more aspects of the present disclosure. The working electrode, the counter electrode and the reference electrode may include arrays of SiNWs that are grown on a silicon chip. The working electrode may be the array of SiNWs electrodes that may be used to attaching cancer cells as described hereinabove in step 302.

It should be understood that the alteration of cancer cell's ionic state, induced by treating the cancer cells with an anticancer drug, can be considered as a criterion to investigate and monitoring the effect of an anticancer drug on cancer cells or in other word, the cancer cells resistance against anticancer drugs as used herein in the present disclosure. As the result, the anticancer drug treatment would change the anodic/cathodic response peaks by releasing cytochrome C in cytoplasm. Reduction of cytochrome C would change the ionic state of the cells attached to the SiNWs electrodes of the biosensor described in the present disclosure. So, the changed electrochemical response of the SiNWs after treating the cells by an anticancer drug could be translated in a well demanded electrochemical approach.

Figure 4:
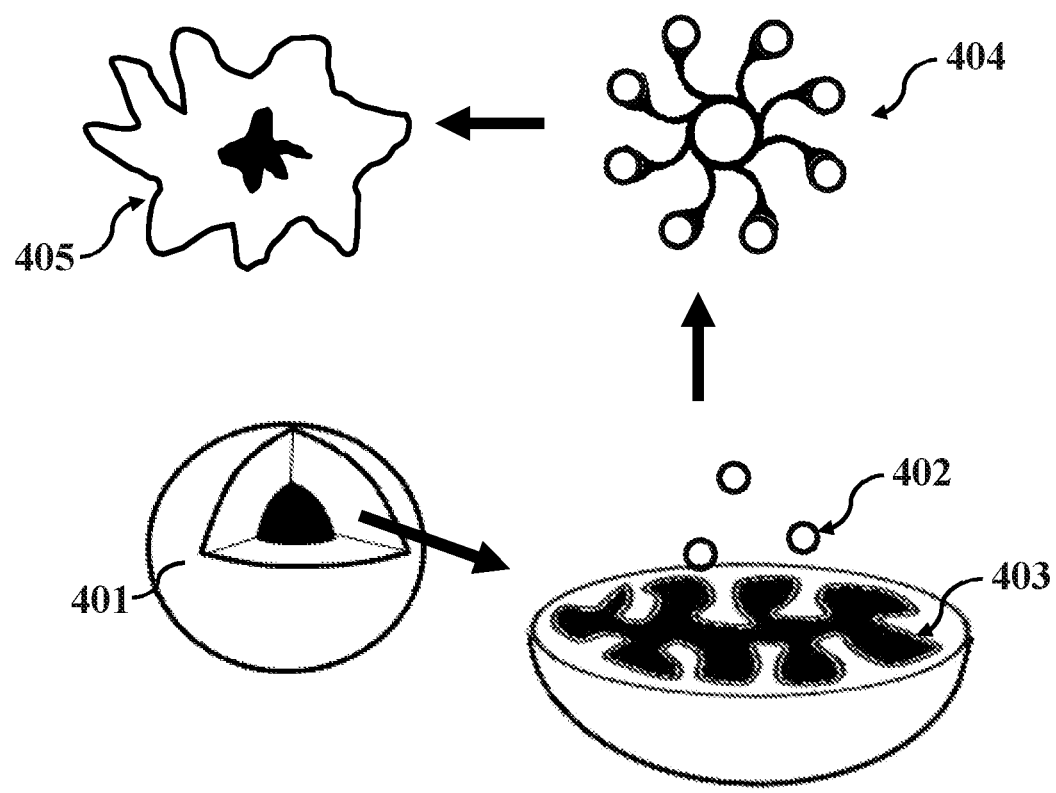
FIG. 4 illustrates an example schematic of the electrochemical affecting of an exemplary anticancer drug on an example cancer cell, consistent with one or more exemplary embodiments of the present disclosure.

FIG. 4 shows a schematic of the electrochemical effect of an example anticancer drug on an example cancer cell, representing the accumulation of cytochrome C from the mitochondria to the cytoplasm resulted in perturbation of the cancer cell's ionic or electrochemical state, consistent with one or more exemplary embodiments of the present disclosure. As shown in this figure, an exemplar MCF-7 cancer cell 401 might be treated by an exemplar MBZ anticancer drug. As a result, the cytochrome C 402 (as an active ionic agent (oxidative)) may be released from the mitochondria 403 and accumulated into the cytoplasm region (such as configuration 404 shown in FIG. 4) that would change the ionic state of cytoplasm and subsequently the ionic equilibrium between cell's inner and outer parts resulted in perturbation of the cell's ionic or electrochemical state. After about 12 hours from this accumulation, activation of caspase-9 and caspase-8 and cleavage of the caspase substrate poly(ADP-ribose) polymerase and procaspase-3 may be detectable. Ultimately, a cell death 405 may be occurred after a time interval of drug treatment. Accordingly, the difference between the first and the second electrochemical (anodic/catholic) responses of the cells attached to the SiNWs before and after the drug treatment may be used to monitor and investigate the anticancer drugs effect on the cancer cells as described in the present disclosure.

EXAMPLES

Example 1

Fabricating a SiNW-Based Biosensor

In this example, a silicon wafer substrate may be cleaned through a standard RCA #1 method (using a $NH_4OH:H_2O_2:H_2O$ solution with a volume ratio of about 1:1:5). The surface of the wafer may be then passivated by a thin layer (having a thickness of about 300 nm) of $SiO_2$ grown by wet oxidation furnace. A gold catalyst layer with a thickness of about 5 nm may be deposited on the $SiO_2$ layer using a sputtering system at a pressure of about 20 m Torr. The Au-covered wafer may be located in a low pressure chemical vapor deposition (LPCVD) system with a quartz tube chamber and the gold may be patterned by architecture of the integrated work, counter and reference electrodes. During a graining process, a thermal annealing at 450-550° C. for 30 min at the presence of argon (Ar) may be carried out which results in the catalyst graining and formation of gold nano-sized islands. The radius of the work electrode (WE) may be about 35 μm. Afterwards, during a growth step, a mixture of high purity silane ($SiH_4$) as Si source and Ar as carrier and dilution gases may be introduced to the chamber. Silicon crystalline nanostructures may be formed on top of the catalyst islands in the patterned regions followed by breaking of the silane to Si and Si—H free radicals.

Figure 5A:
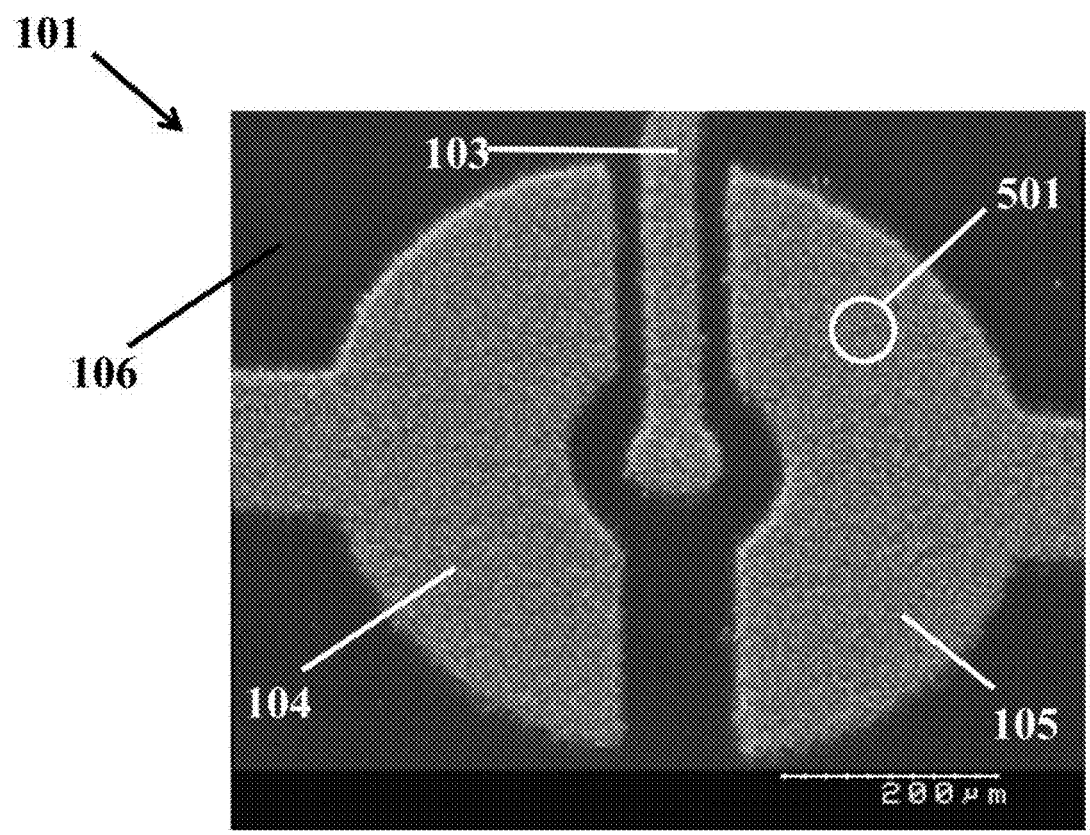
FIG. 5A illustrates a field emission scanning electron microscope (FESEM) micrograph of an example of an integrated SiNW-based sensor including the work, counter and reference electrodes, consistent with one or more exemplary embodiments of the present disclosure.

FIG. 5A shows a field emission scanning electron microscope (FESEM) micrograph of an example of an integrated SiNW-based sensor 101 designed and fabricated in the present exemplary embodiment that may include a work electrode 103, a counter electrode 104 and a reference electrode 105 that may be three arrays of SiNWs grown on a silicon chip 106, in accordance with FIG. 1 described hereinabove. It can be observed from FIG. 5A that SiNWs are present only in the patterned regions associated with the three biosensor electrodes and also have a uniform distribution.

Figure 5B:
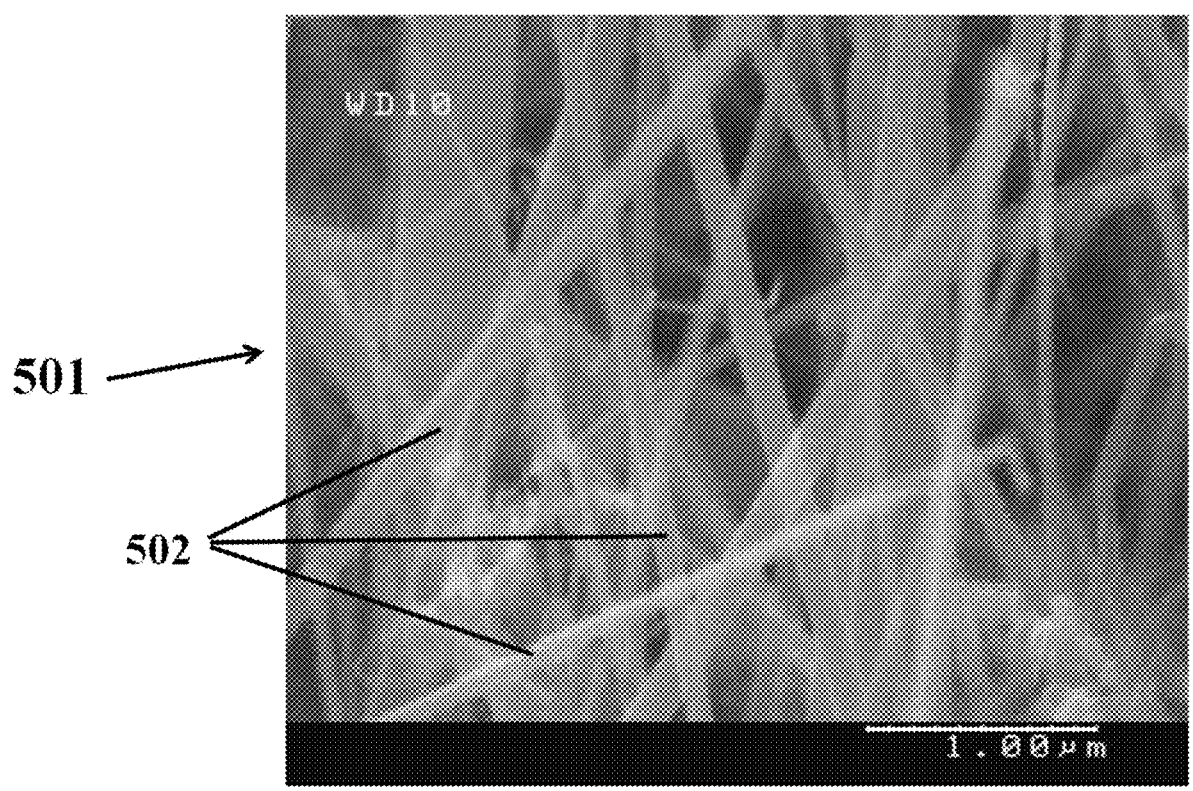
FIG. 5B illustrates a field emission scanning electron microscope (FESEM) micrograph of an example of magnified grown SiNWs of an integrated SiNW-based sensor, consistent with one or more exemplary embodiments of the present disclosure.

FIG. 5B shows a field emission scanning electron microscope (FESEM) micrograph of an example magnified section 501 in FIG. 5A, which may be placed within the grown SiNWs arrays (herein within the reference electrode 305). An array of SiNWs 502 can be observed in this figure including a plurality of silicon nanowires with a width of less than about 80 nm. The morphology and configuration of the SiNWs 502 may form a nest-like porous nanostructure with non-preferential orientations with respect to surface of the substrate (FIG. 5B). Such morphology would provide unique electrochemical characteristics due to their high surface area and excellent ability of their boundaries in sensing any electrochemically produced charges through the crystally connected net of wires.

Figure 5C:
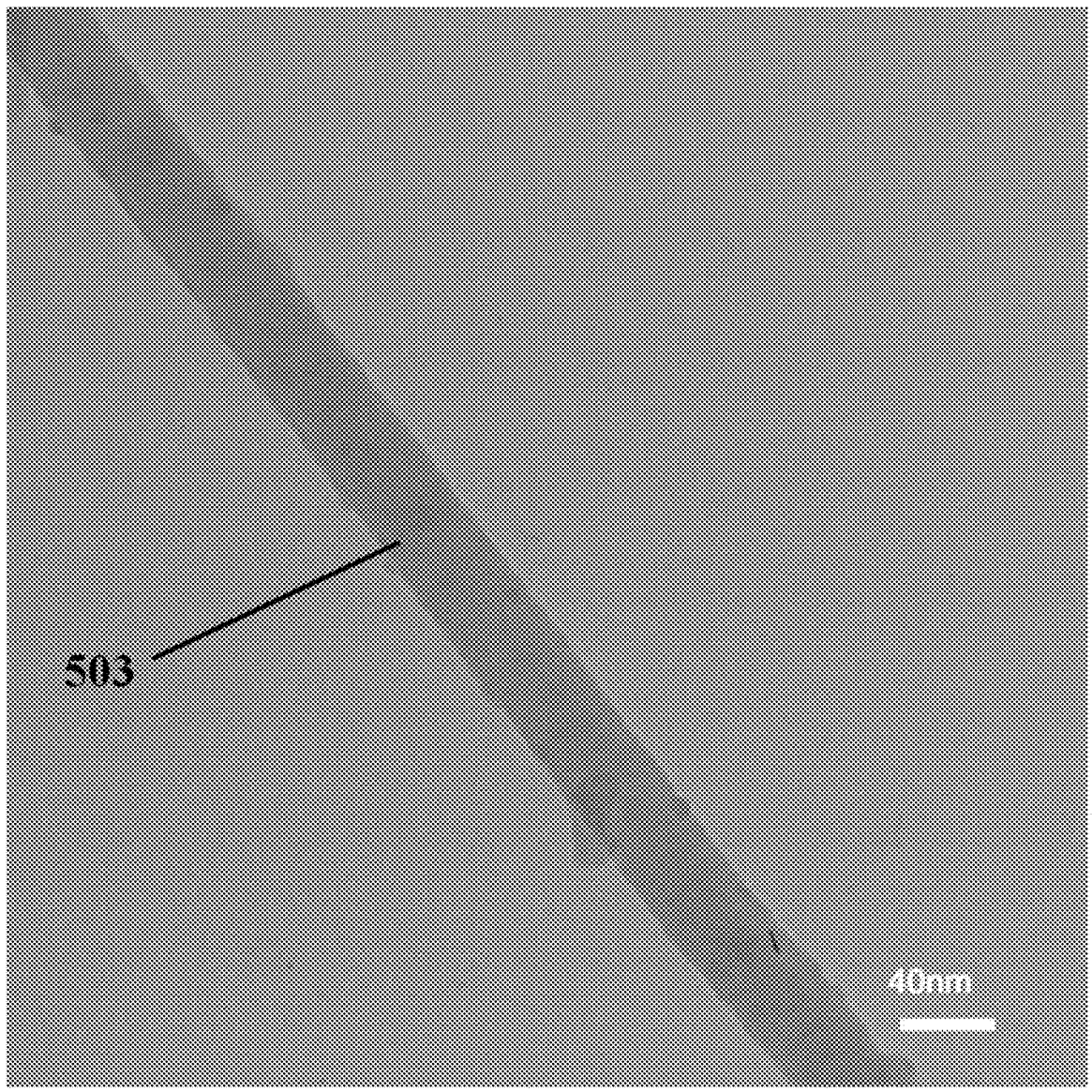
FIG. 5C illustrates a transmission electron microscope (TEM) image of an example of a single silicone nanowire (SiNW) among an array of SiNWs grown on the patterned regions of the catalyst layer, consistent with one or more exemplary embodiments of the present disclosure.

Also, a transmission electron microscope (TEM) image of an example of a single silicone nanowire (SiNW) 503 among the array 502 is shown in FIG. 5C which has a width of about 40 nm.

Figure 5D:
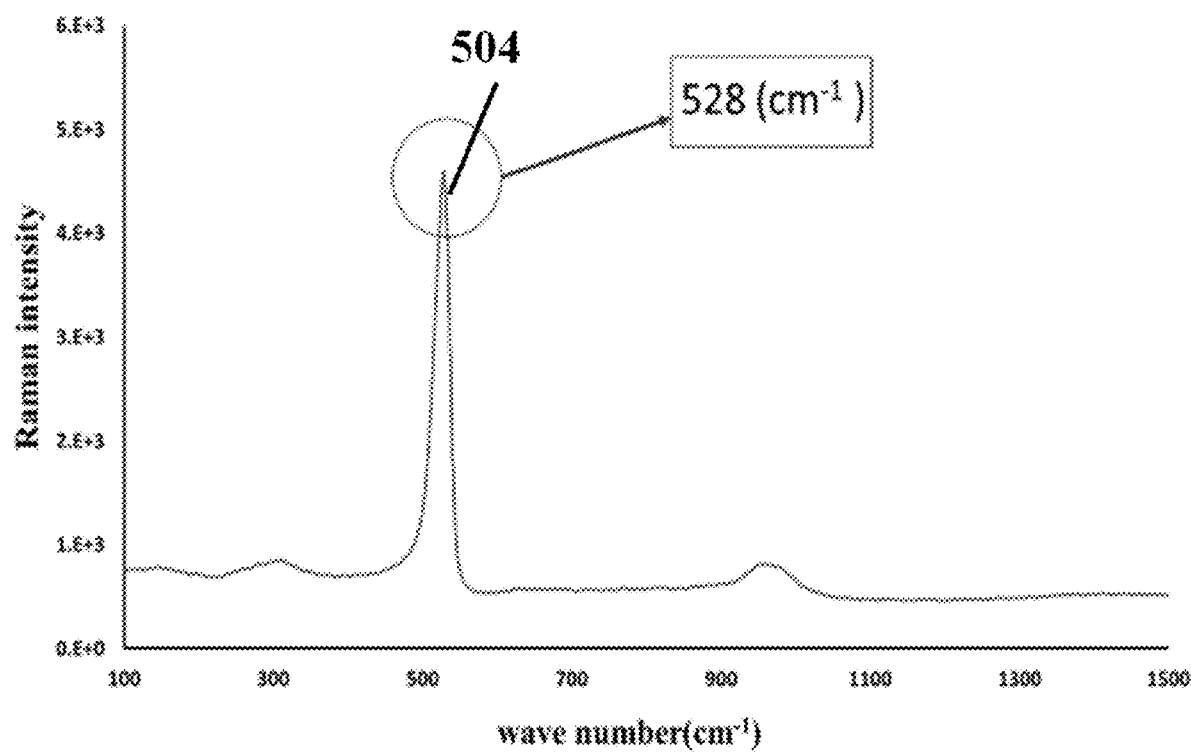
FIG. 5D illustrates a Raman spectroscopy curve of an example of the grown SiNWs, consistent with one or more exemplary embodiments of the present disclosure.

To corroborate the crystalline state of SiNWs which directly affects the SiNWs charge transfer properties, a Raman spectroscopy may be carried out which is shown in FIG. 5D. Observation of a peak 504 of Si at 528 $cm^{-1}$ indicates the crystalline nature of the grown nanowires.

Example 2

Characterization of SiNWs-Based Biosensor

In this example, the SiNW electrodes of an exemplary SiNW-based biosensor of the present disclosure may be analyzed by a cyclic voltammetry (CV) and/or a DPV assay using Ferricyanide as the reference ionic solution and substituting the exemplary biosensor fabricated in connection with Example 1 hereinabove in replace of the electrodes of a cyclic voltammetry system and/or a potentiostat system. Accordingly, the electrodes may be analyzed at a scan rate of about 100 mV/s using a 0.01 M of Ferricyanide ($[Fe(CN)_6]^{3-/4-}$) as reference and standard redox probe.

For CV characterization, three-electrode electrochemical cyclic voltammetry may be performed using the electrochemical workstation. Instead of the system electrodes, the SiNW-based biosensor including integrated SiNW electrodes may be used that is designed and fabricated pursuant to the teachings of the present disclosure. CV assay may be performed between the integrated SiNW covered working electrode 103 and counter electrode 104, with an on chip reference electrode 105 (represented in FIGS. 1 and 5A). The reference electrode may be initially calibrated by an Ag/AgCl reference electrode in a solution of about 1 mM ferrocene carboxylic acid with about 1 mM potassium chloride. CV studies may be performed using DC voltage and applying no AC frequency. For CV data recording, measurements may be carried out at about −0.8 V to 0.8 V at a scan rate of about 100 mv/s.

For DPV measurement, a derivative of linear sweep voltammetry, with a series of regular voltage pulses superimposed on the potential linear sweep. The current may be sampled twice, just before the pulse application and again, late in the pulse lifetime. The current may be measured immediately before each potential change, then the current difference may be plotted as a function of potential. By sampling the current just before the potential was changed, the effect of the charging current may be decreased.

Figure 6A:
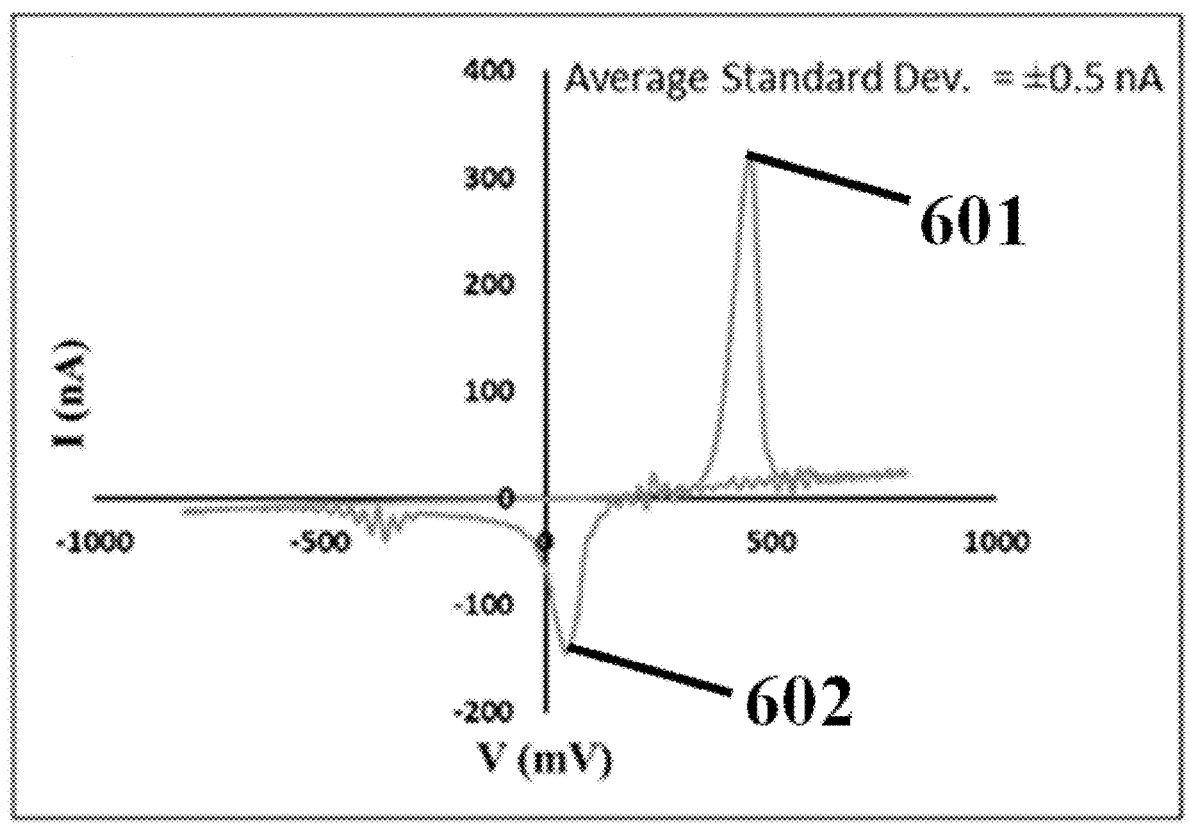
FIG. 6A illustrates a cyclic voltammetry (CV) curve of a Ferricyanide solution measured by an exemplary SiNW-based biosensor used in conjunction with a cyclic voltammetric system, consistent with one or more exemplary embodiments of the present disclosure.

FIG. 6A shows the obtained CV curve for an exemplary fabricated SiNW-based biosensor. The presence of both an anodic current peak 601 (located at 450 mV) and a cathodic current peak 602 (located at 75 mV) of SiNWs electrodes demonstrates the well electrochemical behavior of SiNWs with the great charge transfer mobility of nanowires.

Figure 6B:
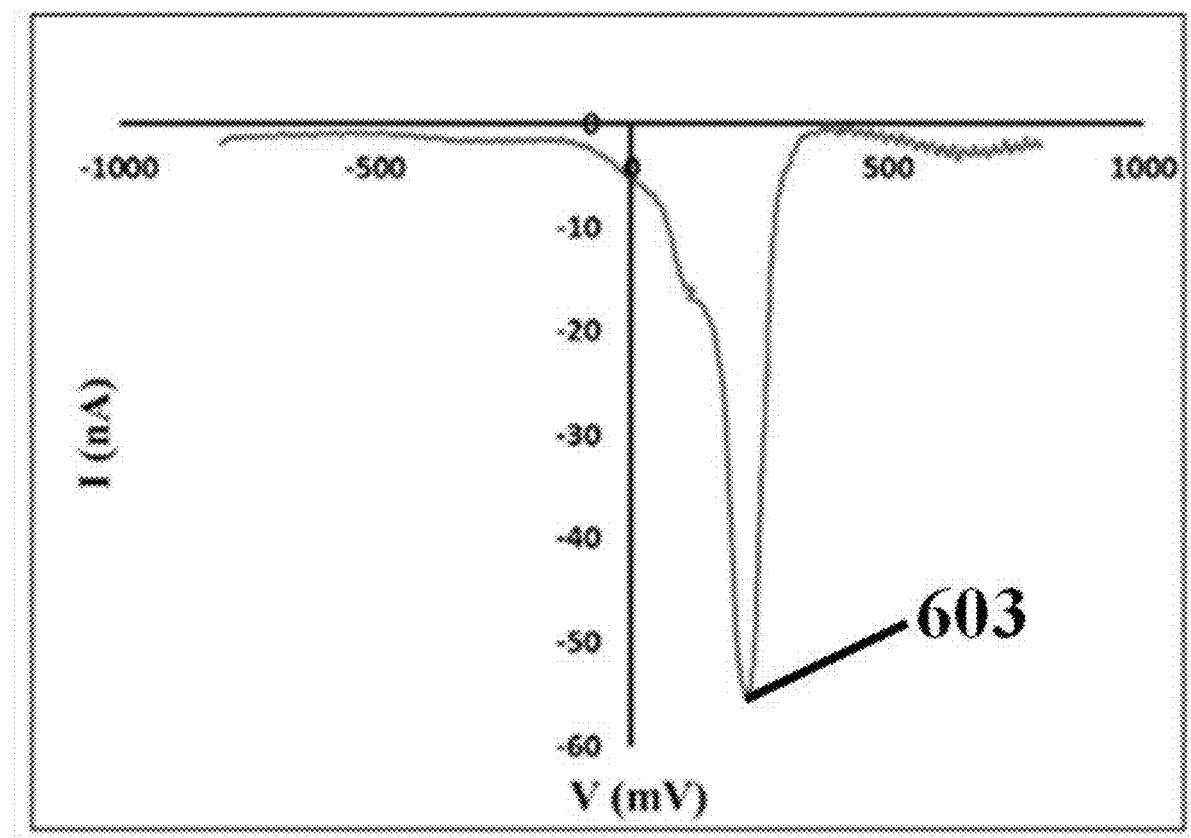
FIG. 6B illustrates a differential pulse voltammetry (DPV) curve of a Ferricyanide solution measured by an exemplary SiNW-based biosensor used in conjunction with a potentiostat system, consistent with one or more exemplary embodiments of the present disclosure.

In addition, FIG. 6B shows an example of the obtained DPV curve for an exemplary fabricated SiNW-based biosensor, wherein the SiNW electrodes are covered with $[Fe(CN)_6]^{3-/4-}$. Reffering to this figure, the DPV response of the $[Fe(CN)_6]^{3-/4-}$ covered SiNW electrodes exhibits a peak current 603 of about −58 nA representing a well electrochemical behavior of SiNWs.

Example 3

Response of the SiNW-Based Sensor to the Presence of Cancer Cells

In this example, to evaluate an exemplary fabricated biosensor of the present disclosure in a cell sensing approach, the CV and DPV responses of the corresponding electrochemical systems may be experimented. The CV and DPV responses may be analyzed for three comparable situations. Initially, in the presence of cells media solution as the crucial ionic environment, then, after attachment of the cells onto the surface of SiNW work electrode and finally, after detachment the cells from the SiNWs by use of a trypsin solution.

During all experiments of the present disclosure, cells should be maintained and incubated in cells media to being alive. The RPMI1640 ionic solution (containing 10% FBS) is a cell culture media that may be used throughout all investigations. So, the electrochemical response of the media should be considered in all of experiments.

Figure 6C:
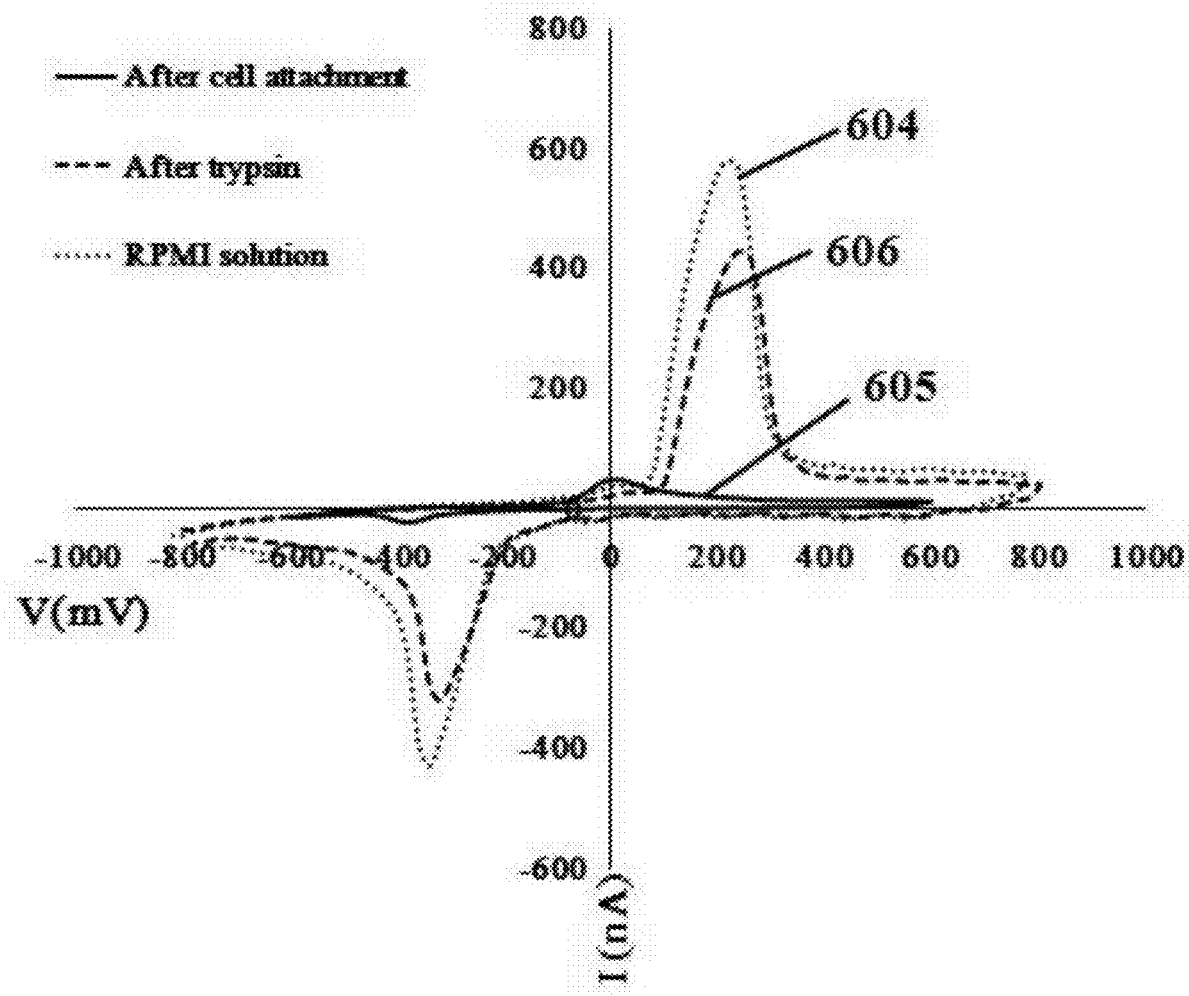
FIG. 6C illustrates cyclic voltammetry (CV) curves of an exemplary SiNW-based biosensor before and after attachment of MCF-7 cells as well as after their detachment from the surface by trypsin, consistent with one or more exemplary embodiments of the present disclosure.

FIG. 6C shows an anodic response of the RPMI detected by SiNW electrodes of an exemplary biosensor designed and fabricated pursuant to the teachings of the present disclosure, that is located at 200 mV (curve 604). High porosity/surface area of SiNWs electrodes can help to increasing the detection resolution of any ionic transfer happened in the sensing media. After attachment of Michigan Cancer Foundation-7 (herein after "MCF-7") cells—that may be used in the present study—on the surface of SiNWs, both anodic and cathodic peaks of the CV response were decreased (curve 605). It would strongly correlate with passivation of the electrodes by the attached cells as dielectric layers. Subsequently, curve 606 presents that the anodic and cathodic spikes may be again observed in the CV response of cells detached SiNWs using a trypsinization process.

Figure 6D:
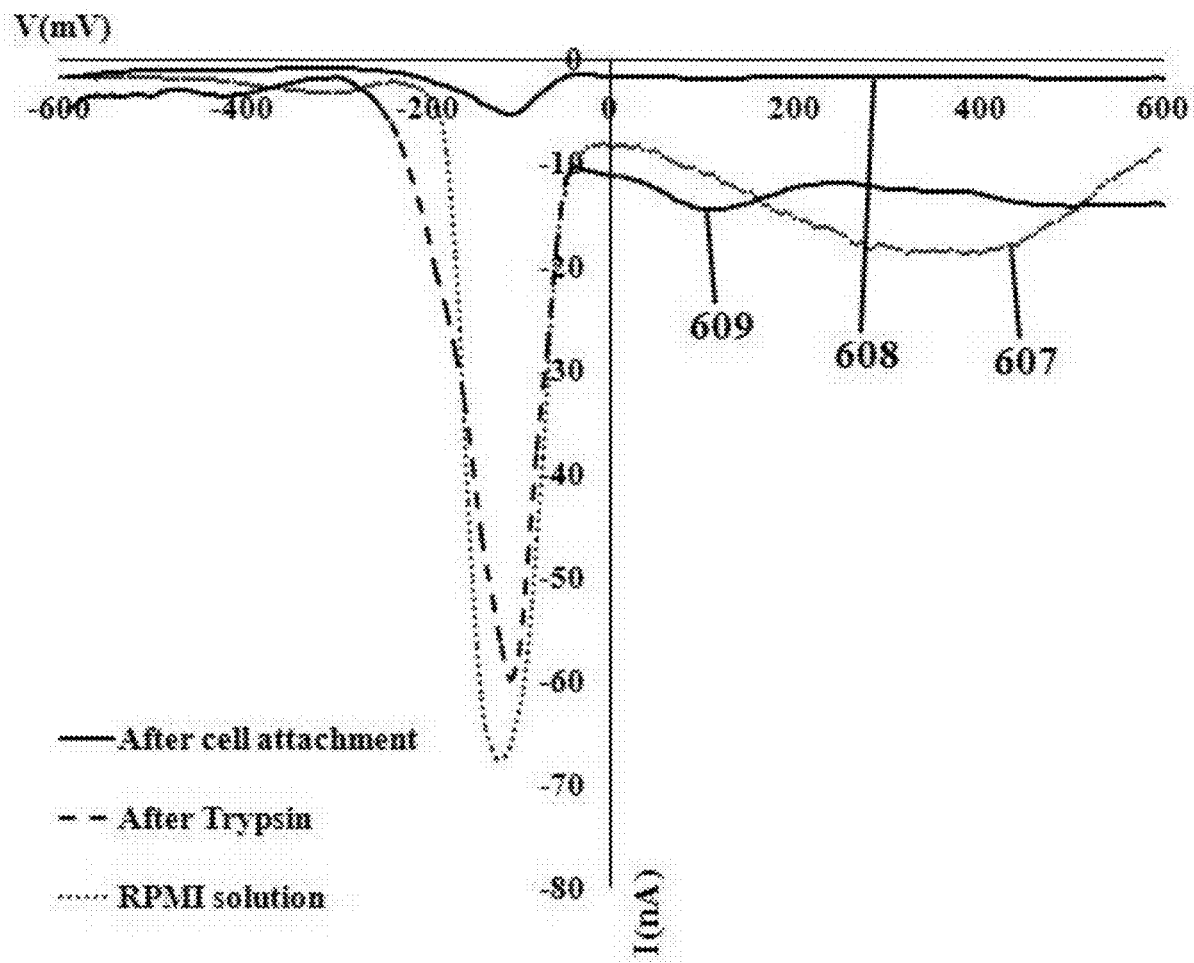
FIG. 6D illustrates differential pulse voltammetry (DPV) curves of an exemplary SiNW-based biosensor before and after attachment of MCF-7 cells as well as after their detachment from the surface by trypsin, consistent with one or more exemplary embodiments of the present disclosure.

FIG. 6D shows DPV profiles of the SiNWs electrodes of an exemplary prepared biosensor pursuant to the teachings of the present disclosure. The intensity of electrochemical DPV peak of RPMI sensed by SiNWs represents a value of about −70 nA (curve 607). The DPV profile of the SiNWs electrodes after attachment of the MCF-7 cells covering all of the effective surface of the work electrode is shown by curve 608. By comparing this voltammogram (curve 608) with DPV spectra of RPMI solution (curve 607), it is observable that the absolute DPV peak current in SiNWs has been reduced about 14 times after attachment of the cells (from about −70 nA to about −5 nA). This would be a well indication on the high interactive surface of SiNWs. The Presence of the cells on the surface of SiNWs suppressed the current flow from WE to CE and degraded the DPV spikes. When detection is not mass transport constrained, only modest enhancement is expected at the lowest concentrations. Finally, the measurements were repeated after detachment of the cells from the surface of SiNW electrodes by trypsinization. It can be seen from curve 609 that the absolute DPV peak current was increased (in negative regime) after detachment of the cells from about 5 nA to about 60 nA. Such increment would be certainly the result of removing the cells as the main agent of suppression in ionic transport between WEs and CEs. We can reveal that the remained adhesive proteins and some residues of the cells after trypsinization from the nanowires might inhibit from the precise adjustment of the peak current in its previous location (curve 609) after detachment of the cells.

Example 4

Shape and Geometry of Cancer Cells Attached on SiNW-Based Biosensor

Figure 7A:
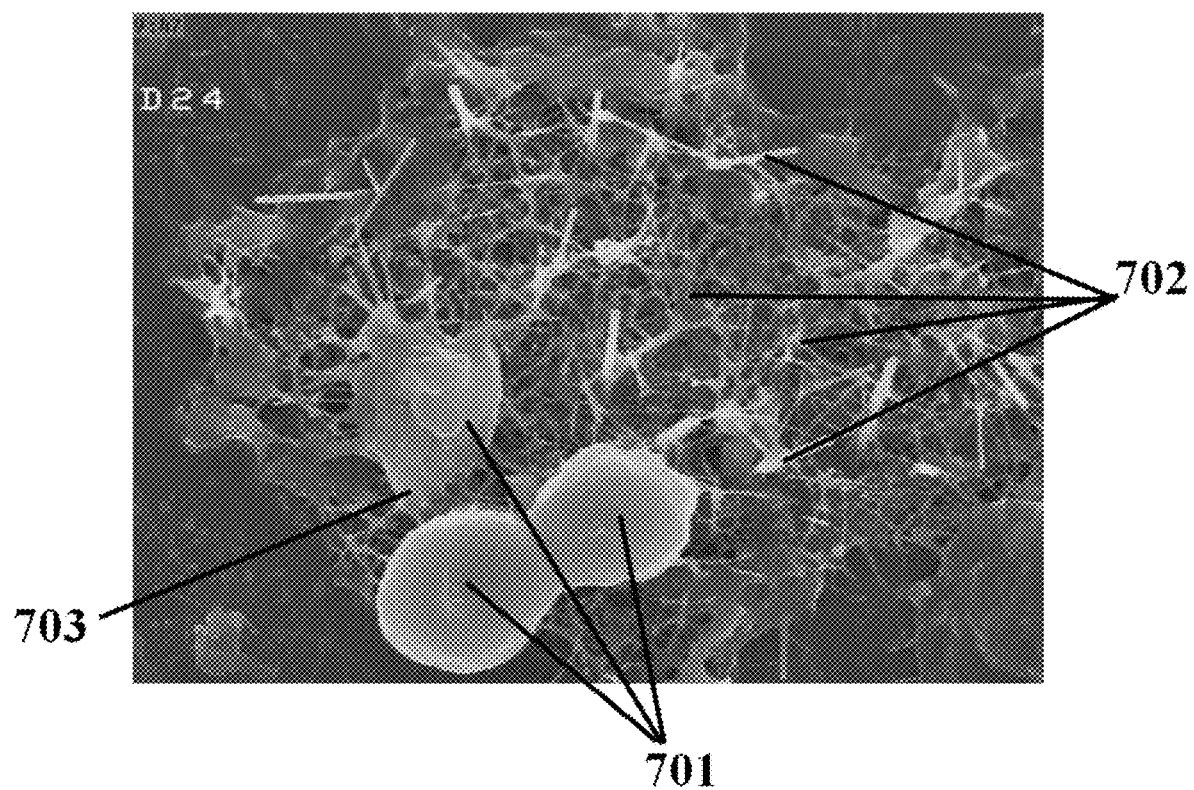
FIG. 7A illustrates a field emission scanning electron microscope (FESEM) micrograph of MCF-7 cells attached on the surface of an example of SiNWs array electrode, consistent with one or more exemplary embodiments of the present disclosure.
Figure 7B:
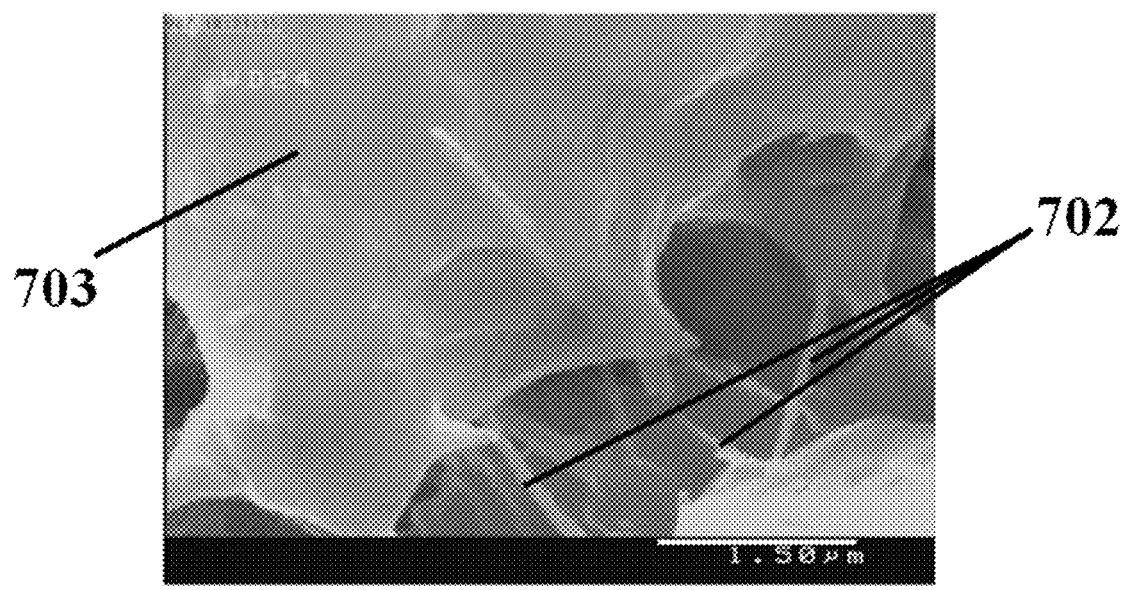
FIG. 7B illustrates a more magnified field emission scanning electron microscope (FESEM) micrograph for an exemplary single MCF-7 cell attached on the surface of SiNWs array of an example of a SiNW-based biosensor, consistent with one or more exemplary embodiments of the present disclosure.
Figure 7C:
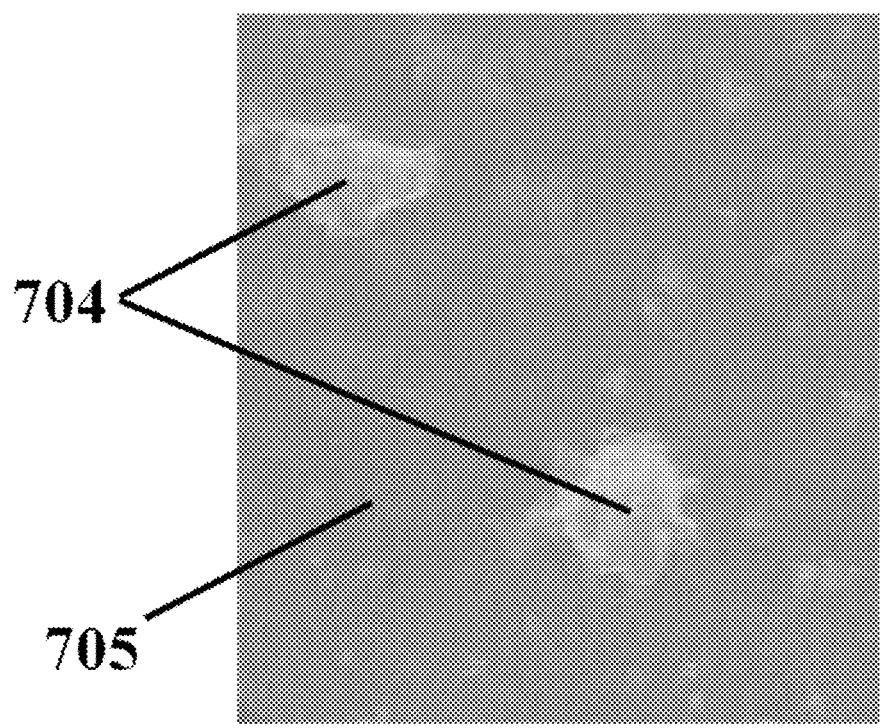
FIG. 7C illustrates a field emission scanning electron microscope (FESEM) micrograph for an exemplary single Michigan Cancer Foundation-7 (MCF-7) cell attached on the surface an exemplary bare Si electrode, consistent with one or more exemplary embodiments of the present disclosure.

FIG. 7A shows a field emission scanning electron microscope (FESEM) micrograph of exemplary MCF-7 cells 701 attached on the surface of an example of SiNWs arrays 702 of an exemplary SiNW-based biosensor of the present disclosure and in connection with the above examples. The width distribution of skein structure of SiNWs ranged from about 45 to about 110 nm induced large efficient interactive surface between a cell and nanowires, that is observable in a more focused FESEM image for an exemplary single cell 703 in FIG. 7B. The efficient interactive surface of SiNWs in the region of single cell is about 22700 μm$^2$ as can be measured from FESEM image of FIG. 7B, meanwhile such surface may be about 127 μm$^2$ for an exemplary cell 704 attached onto an exemplary bare Si electrode 705 that is shown in FIG. 7C. The SiNWs can apply direct interaction with cells because of their attachment into outer membrane all of which considerably enhance the quality of the responses.

Example 5

Anticancer drug Resistance Assay of MCF-7 Cells Using SiNW-Based Biosensor

In this example, the effect of Mebendazole (MBZ), which is an antitubulin drug that induces tubulin depolymerization in cancer cells, may be investigated via an exemplary electrochemical method of the present disclosure. The MCF-7 cells attached on SiNWs of an exemplary biosensor of the present disclosure may be treated with different doses of MBZ and the electrochemical response of an individual non-treated (hereinafter "CTRL") cell and treated cells may be monitored.

Accordingly, exemplary MCF-7 cell lines isolated from grade I human breast tumors may be used as cancer cells. The MCF-7 cells may be maintained in a $CO_2$ incubator containing about 5% $CO_2$ and at a temperature of about 37° C. in a RPMI-1640 medium supplemented with a 5% fetal bovine serum, and 1% penicillin/streptomycin. The fresh medium may be replaced every other day. Prior to each experiment, cells may be trypsinized to be detached from the substrate and re-suspended on the SiNW electrodes of an exemplary biosensor of the present disclosure. To minimize the effect of trypsinization, the procedure may be done in less than about 4 minutes at a room temperature of about 20° C. to about 22° C. The biosensor including the attached cells may be held in an incubator for about 4 hours to achieve cells attachment on the SiNWs. Then the MBZ drug with a low concentration (about 2 nano-mole per liter) and with a high concentration (about 10.5 nano-mole per liter) may be added to the cells. The signal recording and biological assays may be investigated at about 2, 6 and 10 hours after addition of the drug.

Figure 8A:
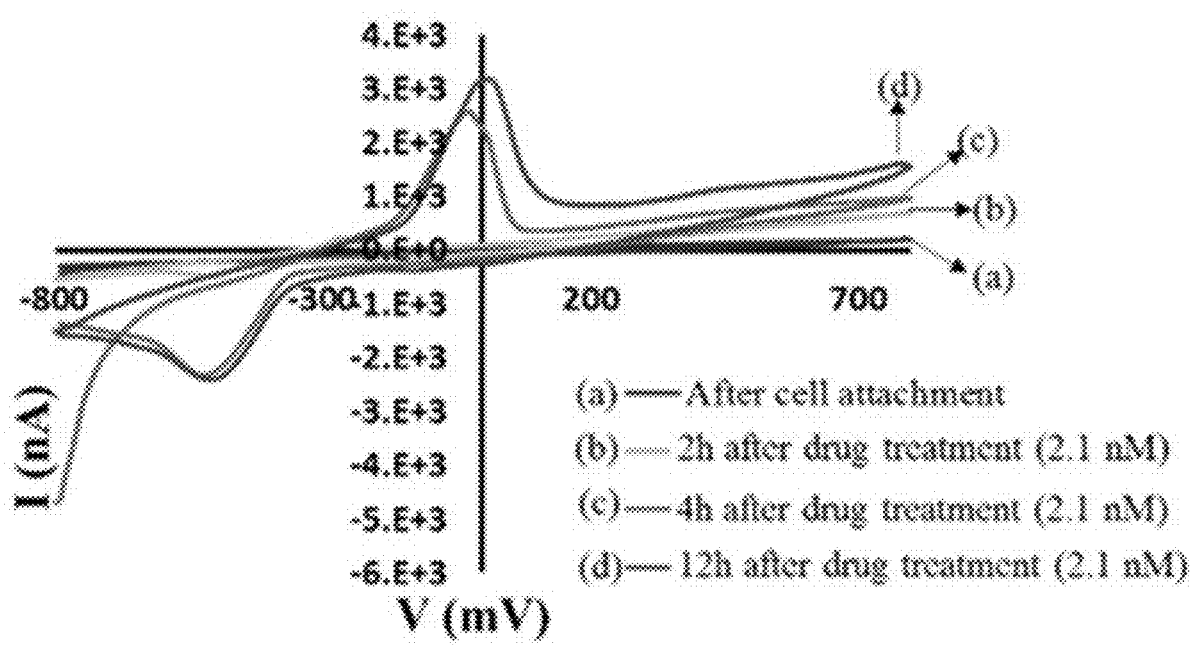
FIG. 8A illustrates cyclic voltammetry (CV) spectra of MCF-7 cells attached on an exemplary SiNW-based biosensor in various time lapses after interaction with 2 nano-mole per liter of MBZ, consistent with one or more exemplary embodiments of the present disclosure.
Figure 8B:
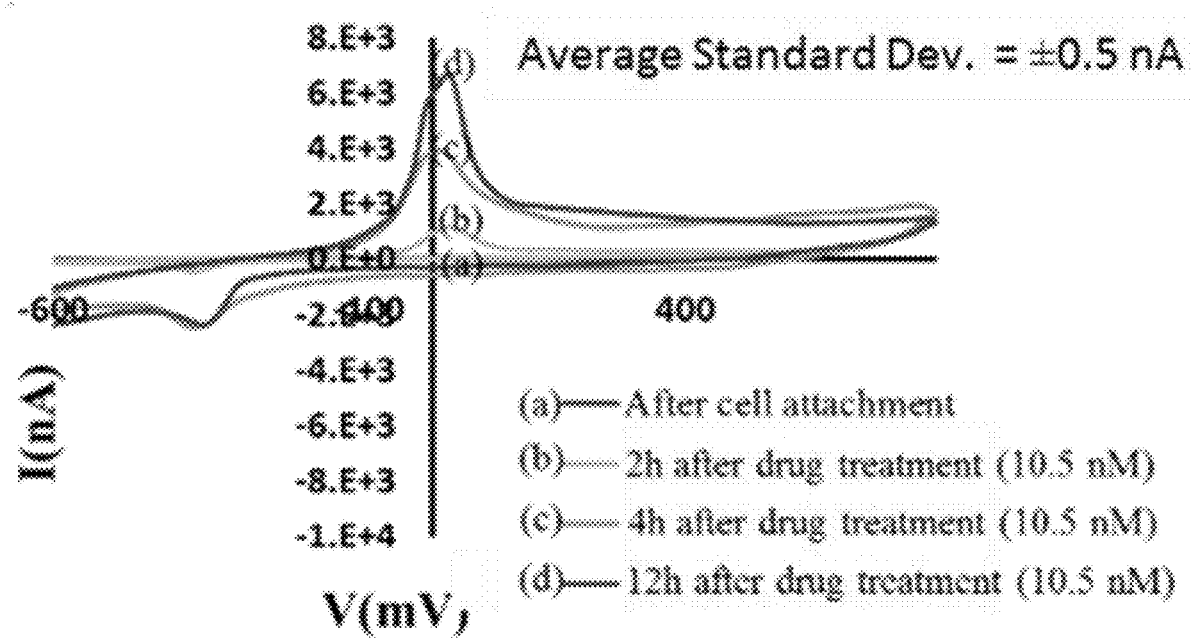
FIG. 8B illustrates cyclic voltammetry (CV) spectra of MCF-7 cells attached on an exemplary SiNW-based biosensor in various time lapses after interaction with 10.5 nano-mole per liter of MBZ, consistent with one or more exemplary embodiments of the present disclosure.

FIGS. 8A and 8B represent the CV diagrams of CTRL and MBZ treated samples with individual MBZ concentrations of about 2 nano-mole per liter (FIG. 8A) and about 10.5 nano-mole per liter (FIG. 8B). Both anodic and cathodic spikes may be observed in CV diagrams just 2 hours after drug incubation with the cells. By increasing the dose of MBZ to about 10.5 nano-mole per liter, the height of the CV spikes increased by nearly three orders (FIG. 8B).

Figure 8C:
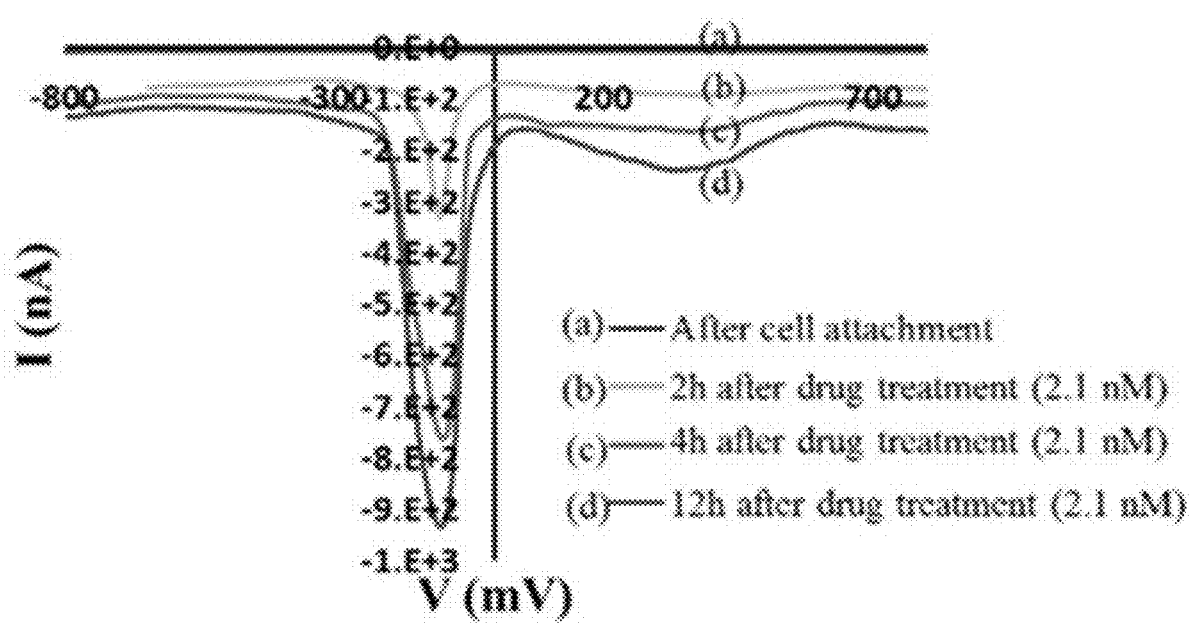
FIG. 8C illustrates differential pulse voltammetry (DPV) spectra of MCF-7 cells attached on an exemplary SiNW-based biosensor in various time lapses after interaction with 2 nano-mole per liter of MBZ, consistent with one or more exemplary embodiments of the present disclosure.
Figure 8D:
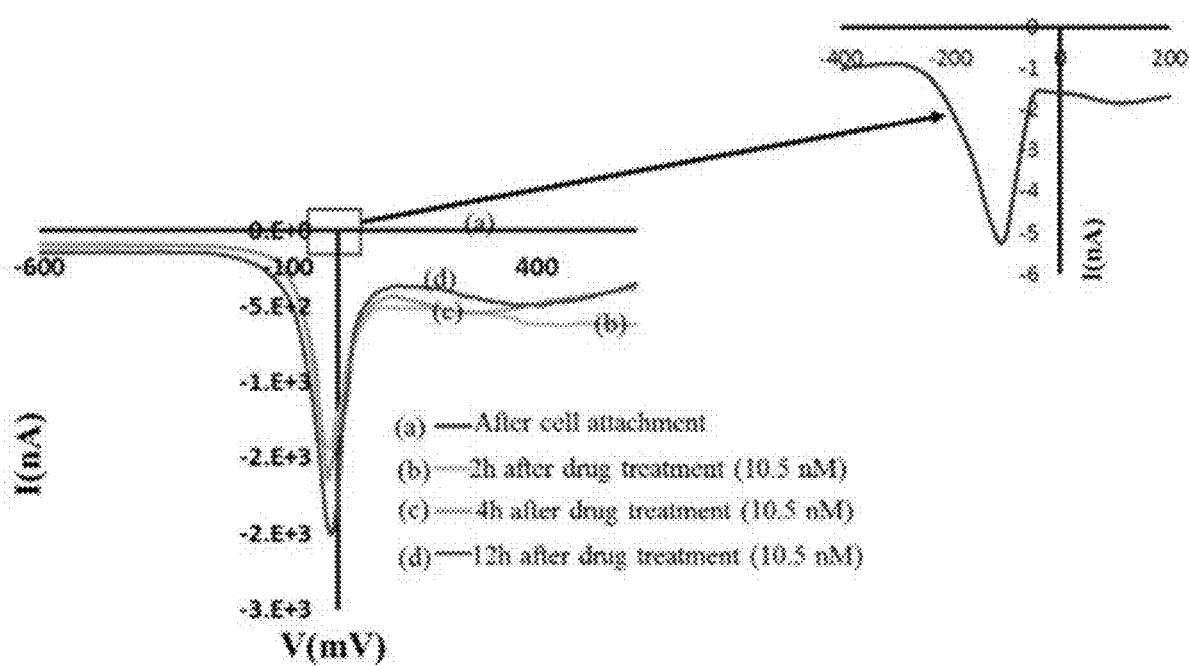
FIG. 8D illustrates differential pulse voltammetry (DPV) spectra of MCF-7 cells attached on an exemplary SiNW-based biosensor in various time lapses after interaction with 10.5 nano-mole per liter of MBZ, consistent with one or more exemplary embodiments of the present disclosure.

Correspondingly, FIGS. 8C and 8D represent the DPV diagrams of CTRL and MBZ treated samples with individual MBZ concentrations of about 2 nano-mole per liter (FIG. 8C) and about 10.5 nano-mole per liter (FIG. 8D). FIG. 8C indicated that just about 2 nano-mole per liter of MBZ may seriously affect the electrochemical response of cancer cells in about 2 hours. Absolute DPV current peaks of the SiNW-based biosensor just 2 hours after cells treatment by about 2 nano-mole per liter of MBZ increased from about 5 nA to about 300 nA. About 12 hours after the treatment, the intensities of the absolute DPV peaks reached to about 900 nA. Absolute DPV of higher dose MBZ (about 10.5 nano-mole per liter) treated cells increased to about 1400 after 2 hours and to about 2000 nA and 12 hours (FIG. 8D).

The Sharp electrochemical response of the MBZ treated MCF-7 cells might be assigned to cells functional perturbations caused by drug induced Microtubule depolymerization. The great charge mobility among the net of silicon nanowires, the excellent capability for exchange of electrons at the nanowalls, the ballistic mobility of electrons in silicon nanocrystalline structure and/or direct attachment of thin rounded nanowalls into the cells might all be effective in the well response of SiNWs electrodes to electrochemical variations in drug-treated cancer cells.

Figure 9A:
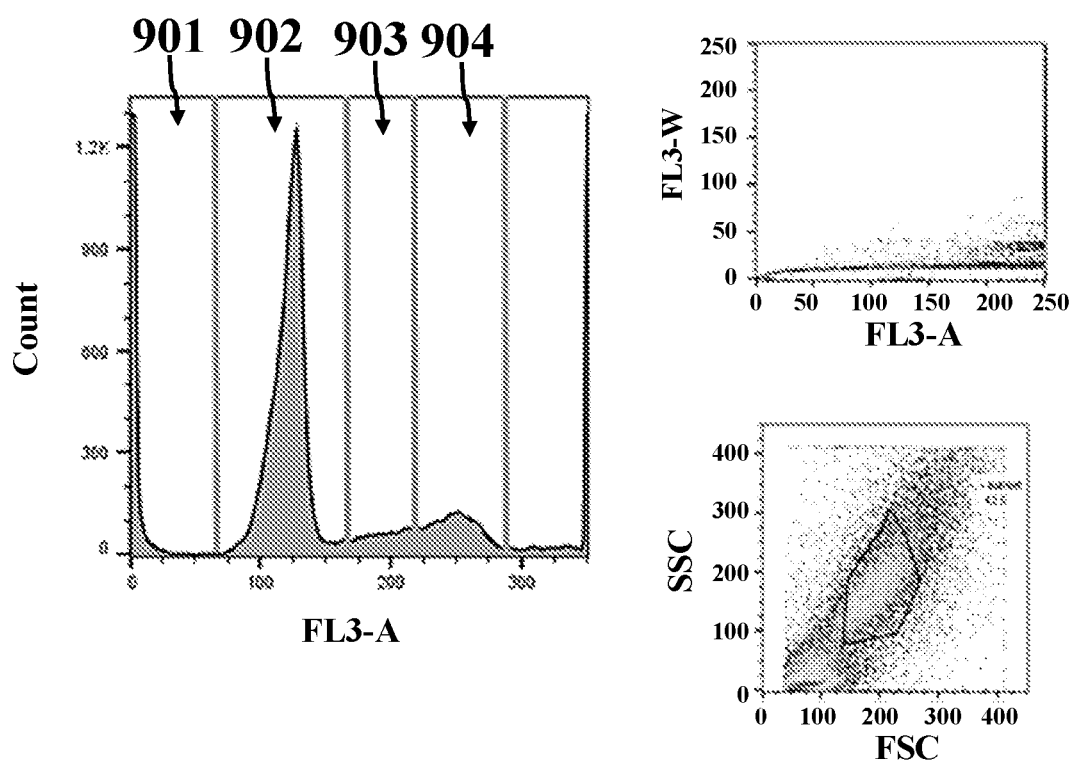
FIG. 9A illustrates flowcytometry analysis curve (Left side) and the state of counted cells (Right side) of MCF-7 cells in the absence of an anticancer drug.
Figure 9B:
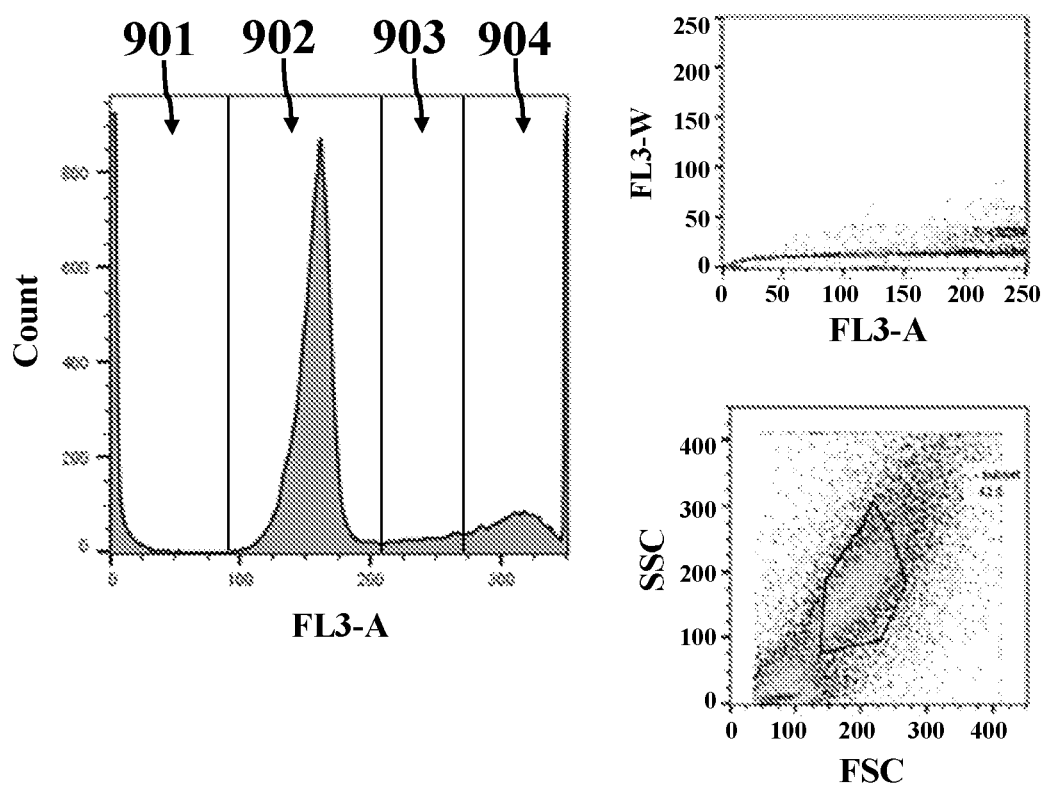
FIG. 9B illustrates flowcytometry analysis curve (Left side) and the state of counted cells (Right side) of MCF-7 cells treated with MBZ with a concentration of about 2 nano-mole per liter.
Figure 9C:
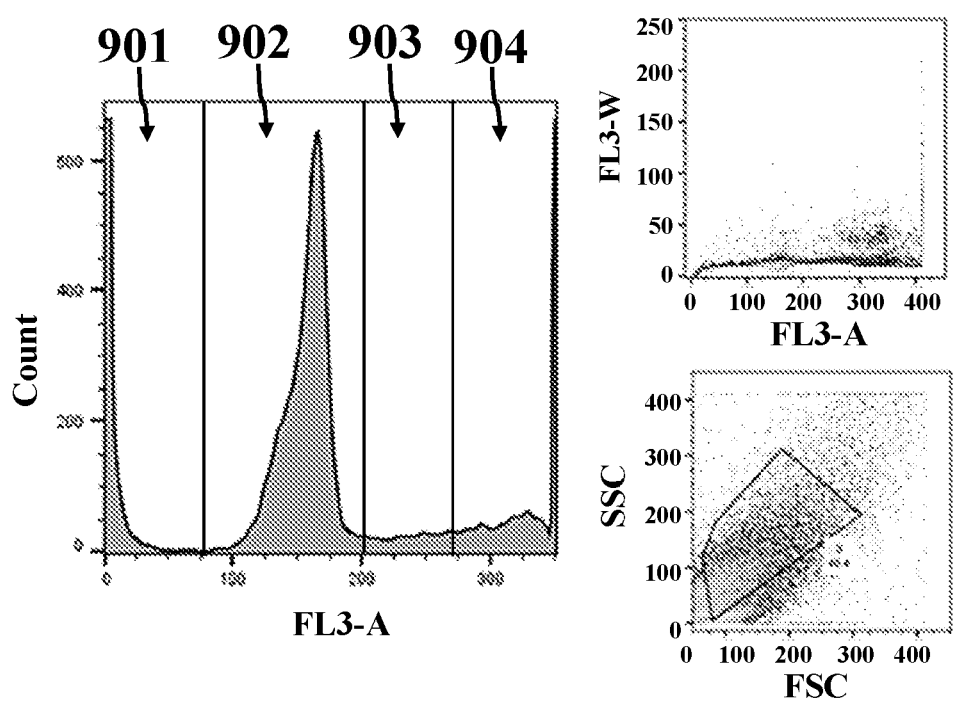
FIG. 9C illustrates flowcytometry analysis curve (Left side) and the state of counted cells (Right side) of MCF-7 cells treated with MBZ with a concentration of about 10.5 nano-mole per liter.

In addition, cell cycle progression for CTRL and drug treated MCF-7 cells may be determined by flowcytometry analysis that are shown in FIG. 9A (for CTRL cells), FIG. 9B (for treated cells with about 2 nano-mole per liter of MBZ) and FIG. 9C (for treated cells with about 10.5 nano-mole per liter of MBZ). The cell's fractions in apoptotic (part 901), G0/G1 (part 902), S (part 903) and G2/M (part 904) cycles are observable in all of panels. Also, the state of counted cells for each of these three situations is represented at the Right side of the figures. These figures show that various concentrations of MBZ induced non similar effects on the cycles and states of the cells. The part 901 representing apoptotic cells with hypodiploid DNA (subG1 fraction) has been slightly increased in low concentration drug treated sample (FIG. 9B) comparing with CTRL sample (FIG. 9A). This reveal that MBZ (about 2 nano-mole per liter) did not induce the apoptotic behavior of MCF-7 cells. But, proportion of G0/G1 fraction (part 902) was changed in MBZ incubated samples. The peak of G0/G1 was about 1300 in CTRL sample (FIG. 9A) meanwhile it was reduced to about 800 in MBZ (about 2 nano-mole per liter) treated cells (FIG. 9B). The result can be confirmed by side scatter versus forward scatter (SSC-FSC) diagram as a strong sign of cells granularity (represented at Right side of FIGS. 9A, 9B and 9C). In addition, the G2/M fraction (part 904) in MBZ (about 2 nano-mole per liter) treated sample shown in FIG. 9B is less than half of measured for CTRL (FIG. 9A). By increasing the dose of MBZ to about 10.5 nM (FIG. 9C), apoptotic behavior (part 901) of the cells was affected. Also, sharper reduction in the amount of the cells in G0/G1 phase (part 902) was observed in similar time. Such disorders in the cycle of the cells after MBZ treatment would be well demanded by affected anodic/cathodic response of the cells measured by SiNWs electrodes.

What is claimed is:

1. A biosensor for measuring an electrical response from a biological sample, the biosensor comprising:
    a substrate;
    a passivation layer, the passivation layer comprising an electrical passivating layer grown on a surface of the substrate;
    a patterned catalyst layer comprising a patterned catalyst layer deposited on the passivation layer; and
    three electrodes grown on the patterned catalyst layer, the three electrodes comprising:
        a working electrode comprising a first array of electrically conductive biocompatible nanostructures, configured to be an attachment site for the biological sample;
        a counter electrode comprising a second array of electrically conductive biocompatible nanostructures, configured to acquire the electrical response from the working electrode; and
        a reference electrode comprising a third array of electrically conductive biocompatible nanostructures, configured to adjust a specific voltage around the working and the counter electrodes,
        wherein the electrically conductive biocompatible nanostructures comprise at least one of silicon nanowires (SiNWs), silicon nanograss, carbon nanotubes (CNTs), and combinations thereof.

2. The biosensor according to claim 1, wherein the substrate comprises a layer of silicon (Si).

3. The biosensor according to claim 1, wherein the passivation layer comprises a layer of silicon dioxide ($SiO_2$) with a thickness in a range between 100 nm and 500 nm.

4. The biosensor according to claim 1, wherein the patterned catalyst layer comprises a layer of at least one of nickel (Ni), gold (Au), iron (Fe), and combinations thereof.

5. The biosensor according to claim 1, wherein the patterned catalyst layer comprises a layer of a catalyst with a thickness of less than 10 nm for growing electrically conductive biocompatible nanostructures thereon.

6. The biosensor according to claim 1, wherein the patterned catalyst layer comprises one of a circular-patterned catalyst layer and an interdigital-patterned catalyst layer.

7. The biosensor according to claim 6, wherein the circular-patterned catalyst layer comprises:
    a first semi-circular layer of the catalyst, deposited and patterned on the passivation layer, the first semi-circular layer of the catalyst configured to grow the second array of electrically conductive biocompatible nanostructures thereon;
    a second semi-circular layer of the catalyst, deposited and patterned on the passivation layer in front of the first semi-circular layer of the catalyst, the second semi-circular layer of the catalyst configured to grow the third array of electrically conductive biocompatible nanostructures thereon; and
    a circular layer of the catalyst, deposited and patterned on the passivation layer between the first semi-circular layer of the catalyst and the second semi-circular layer of the catalyst, the circular layer of the catalyst configured to grow the first array of electrically conductive biocompatible nanostructures thereon.

8. The biosensor according to claim 6, wherein the circular-patterned catalyst layer comprises:
    a circular layer of the catalyst, deposited and patterned on the passivation layer, the circular layer of the catalyst configured to grow the first array of electrically conductive biocompatible nanostructures thereon;
    a partially annular layer of the catalyst, deposited and patterned on the passivation layer around the circular layer of the catalyst, the partially annular layer of the catalyst configured to grow the second array of electrically conductive biocompatible nanostructures thereon; and
    a reference-site layer of catalyst, deposited and patterned on the passivation layer adjacent to the circular layer of the catalyst and the partially annular layer of the catalyst, the reference-site layer of the catalyst configured to grow the third array of electrically conductive biocompatible nanostructures thereon.

9. The biosensor according to claim 6, wherein the interdigital-patterned catalyst layer comprises:
    a first teeth-shaped array of the catalyst layer, deposited and patterned on the passivation layer, the first teeth-shaped array of the catalyst layer configured to grow the first array of electrically conductive biocompatible nanostructures thereon;
    a second teeth-shaped array of the catalyst layer, deposited and patterned on the passivation layer, the second teeth-shaped array of the catalyst layer configured to grow the second array of electrically conductive biocompatible nanostructures thereon; and
    a singular layer of the catalyst, deposited and patterned on the passivation layer adjacent to the first teeth-shaped array of the catalyst layer and the second teeth-shaped array of the catalyst layer, the singular layer of the catalyst configured to grow the third array of electrically conductive biocompatible nanostructures thereon,
    wherein the first teeth-shaped array of the catalyst layer and the second teeth-shaped array of the catalyst layer are placed inside each other.

10. The biosensor according to claim 9, wherein each of the first teeth-shaped array of the catalyst layer and the second teeth-shaped array of the catalyst layer comprises an array of teeth-shaped catalyst layer with a distance between 5 μm and 200 μm for each respective two teeth patterned next to each other.

11. The biosensor according to claim 10, wherein each tooth of the first teeth-shaped array of the catalyst layer and the second teeth-shaped array of the catalyst layer comprises a tooth with a width between 5 μm and 200 μm.

12. The biosensor according to claim 11, wherein:
each tooth of the first teeth-shaped array of the catalyst layer is placed next to at least one tooth of the second teeth-shaped array of the catalyst layer, and
a distance between each tooth of the first teeth-shaped array of the catalyst layer and an adjacent tooth of the second teeth-shaped array of the catalyst layer is the same as the width of each teeth.

13. The biosensor according to claim 1, wherein the SiNWs comprise a plurality of SiNWs with a width of less than 80 nm and a length of less than 50 μm.

14. The biosensor according to claim 1, wherein the CNTs comprise a plurality of vertically aligned multi-walled carbon nanotubes (VAMWCNTs) with a length of between 0.5 μm and 10 μm and a diameter of between 20 nm and 100 nm.

* * * * *